(12) United States Patent
Sherman et al.

(10) Patent No.: US 7,163,794 B2
(45) Date of Patent: Jan. 16, 2007

(54) NUCLEIC ACID BASED NANO-ROBOTIC SYSTEM

(75) Inventors: William B. Sherman, New York, NY (US); Nadrian C. Seeman, New York, NY (US)

(73) Assignee: New York University, New York, NY (US)

( * ) Notice: Subject to any disclaimer, the term of this patent is extended or adjusted under 35 U.S.C. 154(b) by 85 days.

(21) Appl. No.: 10/962,995

(22) Filed: Oct. 13, 2004

(65) Prior Publication Data
US 2005/0136453 A1 Jun. 23, 2005

Related U.S. Application Data

(60) Provisional application No. 60/511,120, filed on Oct. 15, 2003.

(51) Int. Cl.
*C12Q 1/68* (2006.01)
*C12M 1/00* (2006.01)
*G01N 15/06* (2006.01)
*C07H 21/04* (2006.01)

(52) U.S. Cl. .................... 435/6; 435/283.1; 435/287.2; 422/68.1; 536/23.1

(58) Field of Classification Search .................... None
See application file for complete search history.

(56) References Cited

U.S. PATENT DOCUMENTS

2003/0219790 A1* 11/2003 Seeman et al. ................ 435/6

OTHER PUBLICATIONS

Sherman et al "A precisely controlled DNA biped walking device" Nano Letters, 2004, 4(7): 1203-1207.*
Shin et al "A synthetic DNA walker for molecular transport" J. Amer. Chem. Soc., 2004, 126: 10834-10835.*
* cited by examiner

*Primary Examiner*—Bj Forman
(74) *Attorney, Agent, or Firm*—Browdy and Neimark, PLLC

(57) ABSTRACT

A multiped, capable of traveling in more than one direction along a molecular path in a nano-robotic system where the steps taken by the feet of the multiped are controlled in a sequence specific fashion, is presented. The feet of the multiped dock to footholds on the molecular path via cohesion with "set" molecules and are released from the footholds through the introduction of "unset" molecules that detach or strip away the "set" molecules.

29 Claims, 30 Drawing Sheets

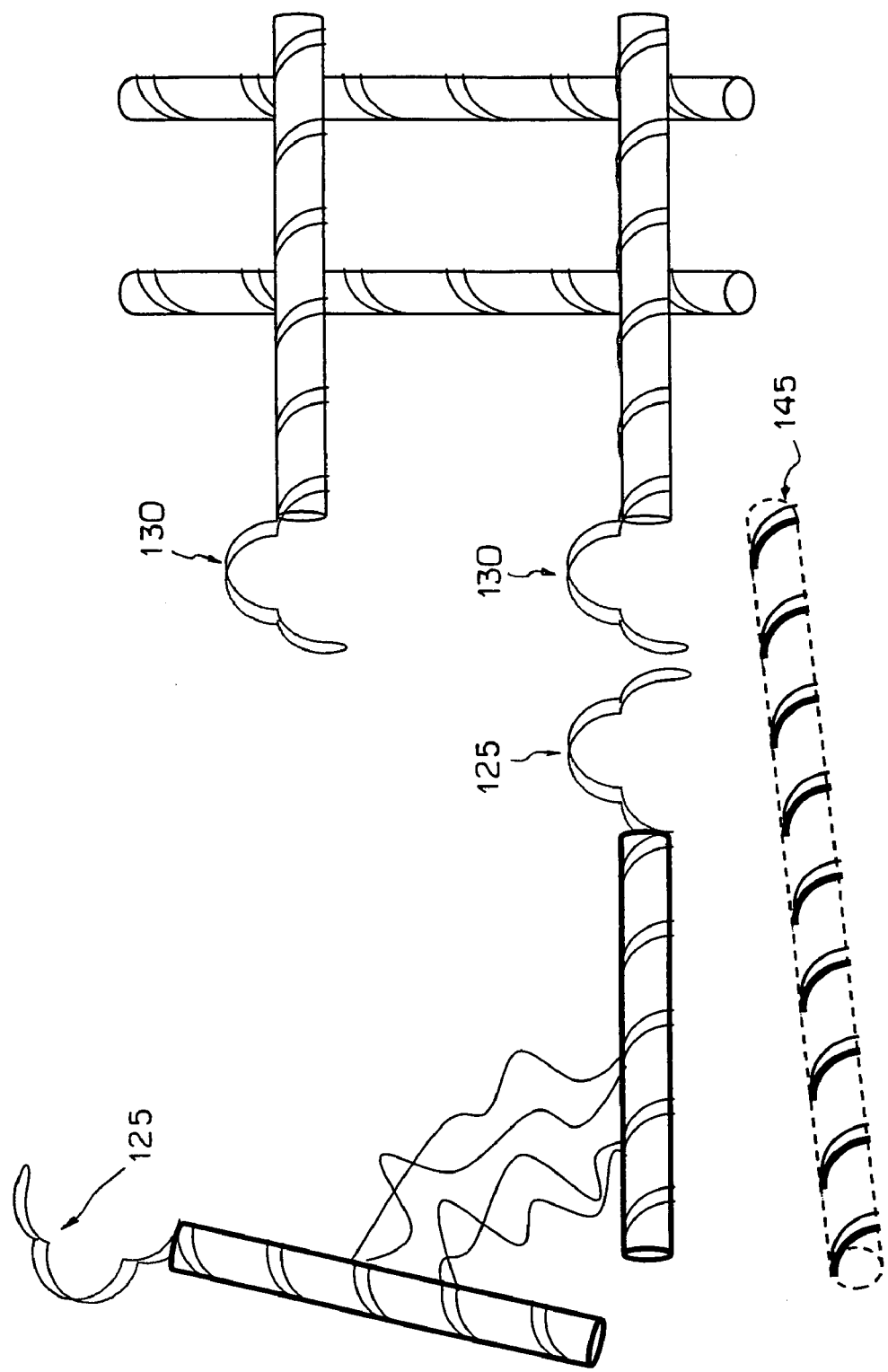

SEQUENCE LISTING

<160> NUMBER OF SEQ ID NOS: 16

<210> SEQ ID NO 1
<211> LENGTH: 71
<212> TYPE: DNA
<213> ORGANISM: Artificial
<220> FEATURE:
<223> OTHER INFORMATION: synthetic
<220> FEATURE:

```
<221> NAME/KEY: misc_feature
<222> LOCATION: (1)..(1)
<223> OTHER INFORMATION: Nucleotide at position 1 is modified with a
      psoralen group.

<400> SEQUENCE: 1
acatctcacg ttaggccatc catactcgag ccgttctctt ttcttatcta gaatgagtga      60
ctgctgcgct g                                                          71

<210> SEQ ID NO 2
<211> LENGTH: 39
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Nucleotide at position 1 is modified with a
      psoralen group.

<400> SEQUENCE: 2
accattagac cagcgcagca tttctttctg atggcctaa                            39

<210> SEQ ID NO 3
<211> LENGTH: 41
<212> TYPE: DNA
<213> ORGANISM: Artificial
<220> FEATURE:
<223> OTHER INFORMATION: synthetic

<400> SEQUENCE: 3
gaacggctcg agtatgtctt cttttgtcac tcattctaga t                         41

<210> SEQ ID NO 4
<211> LENGTH: 65
<212> TYPE: DNA
<213> ORGANISM: Artificial
<220> FEATURE:
<223> OTHER INFORMATION: synthetic

<400> SEQUENCE: 4
gtaaggatag agtggacacc gcagacaagg cgatctggcg ctcctgcctt catgcgtcat     60
agcgt                                                                 65

<210> SEQ ID NO 5
<211> LENGTH: 32
<212> TYPE: DNA
<213> ORGANISM: Artificial
<220> FEATURE:
<223> OTHER INFORMATION: synthetic

<400> SEQUENCE: 5
gcatgaaggc accgatacac tgttattcca gt                                   32

<210> SEQ ID NO 6
<211> LENGTH: 74
<212> TYPE: DNA
<213> ORGANISM: Artificial
<220> FEATURE:
<223> OTHER INFORMATION: synthetic

<400> SEQUENCE: 6
cagtgtatcg gactcctgaa tcacacggat caccaggccg acgagaggac tacttcgatc     60
ctattgtgct ctgt                                                       74
```

<210> SEQ ID NO 7
<211> LENGTH: 55
<212> TYPE: DNA
<213> ORGANISM: Artificial
<220> FEATURE:
<223> OTHER INFORMATION: synthetic

<400> SEQUENCE: 7
ataggatcga agtagtggag tggagcgcca gatcgccttg tctgcggacg ctcgt          55

<210> SEQ ID NO 8
<211> LENGTH: 72
<212> TYPE: DNA
<213> ORGANISM: Artificial
<220> FEATURE:
<223> OTHER INFORMATION: synthetic

<400> SEQUENCE: 8
acgagcgtgg tattttata cctgtcctga tccgtgtgat tcacctctcg tcggcctgga      60
ctctatcctt ac                                                        72

<210> SEQ ID NO 9
<211> LENGTH: 28
<212> TYPE: DNA
<213> ORGANISM: Artificial
<220> FEATURE:
<223> OTHER INFORMATION: synthetic

<400> SEQUENCE: 9
cagccaatcg tgagatgtac gctatgac                                        28

<210> SEQ ID NO 10
<211> LENGTH: 28
<212> TYPE: DNA
<213> ORGANISM: Artificial
<220> FEATURE:
<223> OTHER INFORMATION: synthetic

<400> SEQUENCE: 10
cgcaaggtcg tgagatgtac tggaataa                                        28

<210> SEQ ID NO 11
<211> LENGTH: 28
<212> TYPE: DNA
<213> ORGANISM: Artificial
<220> FEATURE:
<223> OTHER INFORMATION: synthetic

<400> SEQUENCE: 11
ggcgttgagt ctaatggtac tggaataa                                        28

<210> SEQ ID NO 12
<211> LENGTH: 28
<212> TYPE: DNA
<213> ORGANISM: Artificial
<220> FEATURE:
<223> OTHER INFORMATION: synthetic

<400> SEQUENCE: 12
gccgaaccgt ctaatggtac agagcaca                                        28

<210> SEQ ID NO 13
<211> LENGTH: 28
<212> TYPE: DNA

```
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Nucleotide at position 1 is modified with a
      biotin group.

<400> SEQUENCE: 13
gtcatagcgt acatctcacg attggctg                                              28

<210> SEQ ID NO 14
<211> LENGTH: 28
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Nucleotide at position 1 is modified with a
      biotin group.

<400> SEQUENCE: 14
ttattccagt acatctcacg accttgcg                                              28

<210> SEQ ID NO 15
<211> LENGTH: 28
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Nucleotide at position 1 is modified with a
      biotin group.

<400> SEQUENCE: 15
ttattccagt accattagac tcaacgcc                                              28

<210> SEQ ID NO 16
<211> LENGTH: 28
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Nucleotide at position 1 is modified with a
      biotin group.

<400> SEQUENCE: 16
tgtgctctgt accattagac ggttcggc                                              28
```

US 7,163,794 B2

NUCLEIC ACID BASED NANO-ROBOTIC SYSTEM

CROSS-REFERENCE TO RELATED APPLICATION

The present application claims priority under 35 U.S.C. §119(e) from U.S. provisional application Ser. No. 60/511,120, filed Oct. 15, 2003, the entire content of which is hereby incorporated by reference.

GOVERNMENT LICENSE RIGHTS

The experiments performed in this application were supported in part by the National Institutes of Health, grant no. GM-29554, by the Office of Naval Research, grant no. N00014-98-1-0093, by the National Science Foundation, grant nos. CTS-9986512 and EIA-0086015, by the United States Air Force, grant no. F30602-98-C-1048, and by DARPA/NSF grant no. NSF-CCR-97-25021. The U.S. Government has a paid up license in this invention and the right in limited circumstances to require the patent owner to license others on reasonable terms as provided for by the terms of the above grants.

BACKGROUND OF THE INVENTION

1. Field of the Invention

The present invention relates to nanotechnology and to a nucleic acid based nano-robotic system.

2. Description of the Related Art

The laboratory of the present inventors has developed numerous techniques for building complex rigid structures out of DNA. In particular, double crossover (DX) (Li et al., 1996; Liu et al., 1999), triple crossover (TX) (LaBean et al., 2000), parallelogram (Mao et al., 1999a) and 6-tube molecules (Mathieu et al., 2001), all of which can form one and/or two dimensional repeating arrays were developed. In 1999, the laboratory of the present inventors reported the first DNA-based nanomechanical device (Mao et al., 1999b). It was based on the transition of known sequences of DNA to switch from right handed to left handed twists upon addition of a chemical actuator ($Co(NH_3)_6^{+++}$) to the solution. Were one to put, say, 10 different versions of this device into a test-tube, one could still produce only two states, one with all the molecules twisted left, and another with all the molecules twisted right. In 2000, Yurke et al. developed a method for controlling numerous DNA nano-devices in the same test-tube independently. They managed this by making the control molecules DNA strands which hybridize with their complements, but no other molecules. Several groups including ours have produced DNA nano-devices on this theme (Yan et al., 2002; Simmel et al., 2001; Niemeyer et al., 2002). All the DNA nano-devices produced to date, however, have had two limitations. They only can enter a specific, finite, number of states; and those states are all essentially changes in shape of a single macromolecule.

A tremendous literature has arisen exploring numerous protein-based nano-motors (Hess et al., 2002; Soong et al., 2000; Allan et al., 2002). These have certain advantages over conventional DNA nano-devices. Being motors, they have an infinite range of motion (be it rotational or linear), and they consist of two portions—one large static molecule, and one smaller mobile molecule which moves along it. There are, however, disadvantages of protein nano-motors relative to DNA nano-devices. Protein motors only run in one direction, they are difficult to start/stop rapidly and precisely, and all such motors in a given environment will run whenever ATP fuel is made available (they lack the precise interface of DNA coded control strands).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a nano-robotic system in which a multiped can travel along a molecular path. This system includes the multiped and a molecular path as well as a plurality of different sequence specific nucleic acid set and unset molecules that allows the feet of the multiped to dock to or be released from a foothold on the molecular path. The multiped has at least two feet, each of which has a sequence specific nucleic acid end and each of which is joined to at least one other foot on the multiped by a tether. The molecular path has a plurality of sequence specific nucleic acid footholds disposed along the path and onto which each foot of the multiped docks in the presence of a sequence specific nucleic acid set molecule that attaches by cohesion to both the sequence specific nucleic acid end of a foot and the sequence specific nucleic acid foothold. The foot is released from the foothold when a sequence specific nucleic acid unset molecule is introduced which detaches or strips away the set molecule from its cohesion to the foot and foothold.

The present invention is further directed to a method for positioning a foot of the multiped of the nano-robotic system of the present invention from one foothold to another along the molecular path. This method involves the sequential use of set and unset molecules.

BRIEF DESCRIPTION OF THE DRAWINGS

FIG. 1A shows a state (termed 11, 22) in which the biped is attached to two footholds (docks 2 and 3) of a molecular path by two sequence specific nucleic acid set molecules (strands). Set strand 1,1 connects foot 1 to the foothold dock 1 and set strand 2,2 connects foot 2 to the foothold dock 2.

FIG. 1B shows the initial attachment of unset strand 2,2 to the nonhybridized nucleotides (portion 3 or "toehold") of set strand 2,2, which then proceeds to detach or strip away set strand 2,2 from foot 2 and foothold/dock 2.

FIG. 1C shows a state (termed 11) in which set strand 2,2 and unset strand 2,2 are hybridized and foot 2 is now detached from foothold/dock 2. In this 11 state, foot 1 is still attached to foothold/dock 1. The presence of an optional biotin molecule on unset strand 2,2 can be used to remove the hybridized set and unset strands 2,2 using streptavidin coated magnetic beads.

FIG. 1D shows a state termed 11,23 where a set strand 2,3 has been introduced and attaches foot 2 to foothold/dock 3. The flexible tethers between foot 1 and foot 2 are stretched to allow for this attachment.

FIG. 1E shows the initial attachment of unset strand 11 to the nonhybridized nucleotides (portion 3) of set strand 1,1, which then proceeds to detach or strip away set strand 1,1 from foot 1 and foothold/dock 1.

FIG. 1F shows a state termed 23 in which set strand 1,1 and unset strand 1,1 are hybridized and foot 1 is now detached from foothold/dock 1. In this 23 state, foot 2 is attached to foothold/dock 3.

FIG. 1G shows a state termed 12,23 where a set strand 1,2 has been introduced and attaches foot 1 to foothold/dock 2. The biped has now traveled along the molecular path simplistically composed of footholds/docks 1,2 and 3.

FIG. 6A shows attachment of a thick line arm to the biped and FIG. 6B shows that the thick line arm is released from the biped and that the dashed arm is attached to the biped in its place.

FIGS. 9A–9K show a series of schematic illustrations of a biped (with foot 1 and foot 2 tethered together) being released from attachment via paranemic cohesion through a set molecule to footholds on the molecular path using unset molecules as follows:

FIG. 9A shows two set molecules (thick black lines) which attach the feet of the biped to two footholds on the molecular path. The upper set molecule is a circular nucleic acid strand and the lower set molecule is a linear nucleic acid strand.

FIG. 9B shows an unset molecule initiating removal of the set molecule from the upper foot and foothold by forming a paranemic crossover (PX) domain with the toehold of the set molecule.

FIG. 9C shows the set and unset molecules extending their PX domain via a stochastic process analogous to conventional branch migration.

FIGS. 9D and 9E shows further sequential extension of the PX domain of the set and unset molecules with the upper foot of the biped being released from the foothold.

FIG. 9F shows the upper foot released from the foothold with the set molecule fully detached and in paranemic cohesion with the unset molecule.

FIG. 9G shows a single stranded unset molecule initiating the removal of the set molecule from the lower foot and foothold by Watson-Crick sequence complementarity to the single stranded toehold of the set molecule.

FIG. 9H shows the removal of the set molecule through conventional branch migration.

FIGS. 9I and 9J show further sequential branch migration to release the lower foot from the foothold.

FIG. 9K shows the lower foot released from the foothold with the set molecule fully detached and forming a duplex with the unset molecule.

DETAILED DESCRIPTION OF THE INVENTION

Figure 1A:
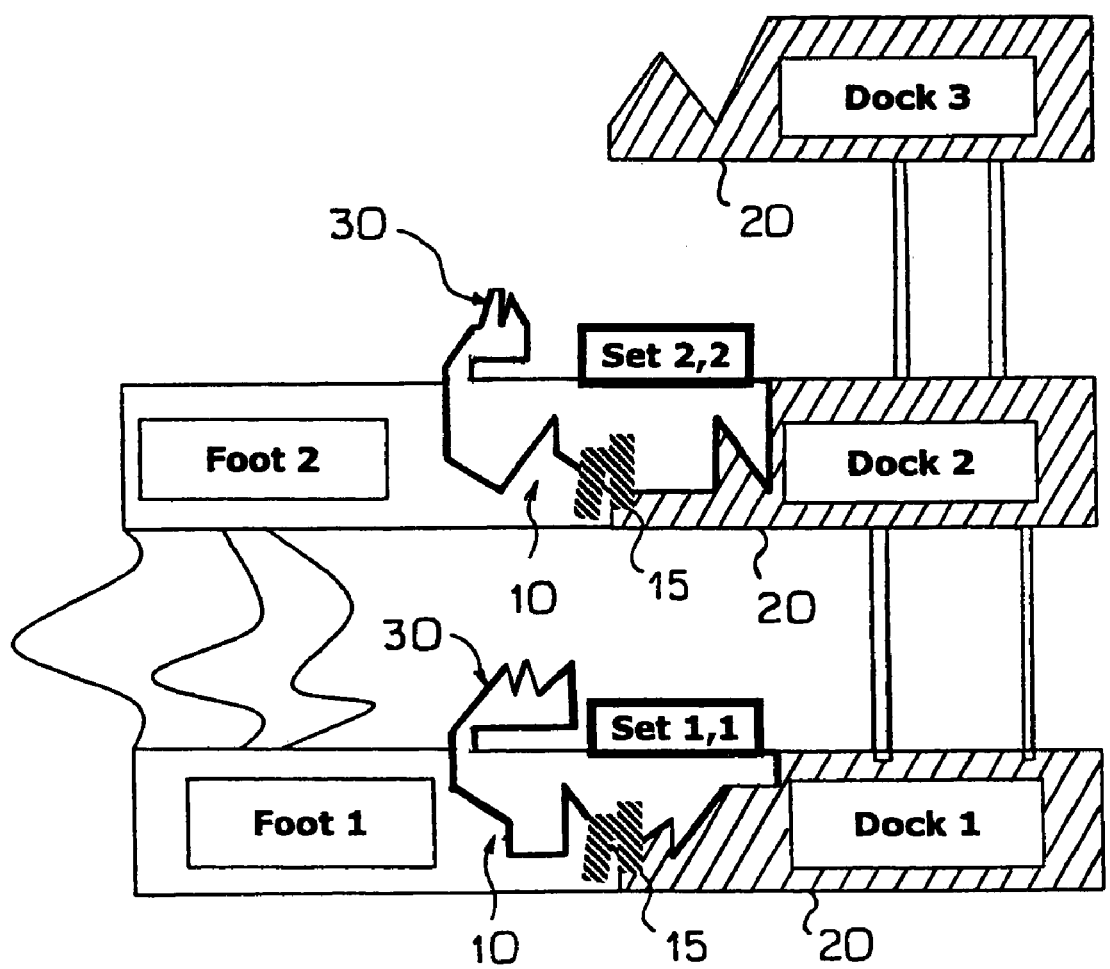
FIGS. 1A–1G show a series of simplistic schematic illustrations of a biped with foot 1 and foot 2 tethered together and traveling from one foothold (dock 1, 2, and 3) to another as follows.

The nano-robotic system developed in the laboratory of the present inventors provides a way for a nano-device to generate movement or displacement relative to a molecular path. This nano-robotic system has the sequence specific control and reversibility of nucleic acid devices but also has essentially an infinite range of motion similar to protein nano-motors.

The nano-robotic system of the present invention includes a molecular multiped, a molecular path along which the multiped can travel in more than one direction, a plurality of different sequence specific nucleic acid set molecules, and a plurality of different sequence specific nucleic acid unset molecules. The molecular multiped has two or more feet with which to "walk" along the molecular path. Each foot of the multiped has a sequence specific nucleic acid end and each foot is joined to at least one other foot of the multiped by a tether. The molecular path includes a plurality of sequence specific nucleic acid footholds disposed along the path. These footholds are the locations on the molecular path where a sequence specific nucleic acid end of a foot of the multiped can be placed or "docked" in the presence of a sequence specific nucleic acid set molecule that attaches by cohesion to both a sequence specific nucleic acid end of a foot of the multiped and a sequence specific nucleic acid foothold of the molecular path. The sequence specific nucleic acid set molecule has the following: (1) a portion which is capable of attaching by cohesion to a sequence specific nucleic acid end of a foot of the multiped; (2) a portion which is capable of attaching by cohesion to a sequence specific nucleic acid foothold of the molecular path; and (3) a portion termed "toehold" which is incapable of separately attaching to either the sequence specific nucleic acid end of a foot of the multiped or the sequence specific nucleic acid foothold of the molecular path to which portion (1) or (2) of said sequence specific nucleic acid set molecule can attach.

A foot that is docked to a foothold by a sequence specific nucleic acid set molecule can be released from the foothold in the presence of a sequence specific nucleic acid unset molecule which detaches or strips away the sequence specific nucleic acid set molecule from the foot and the foothold. The sequence specific nucleic acid unset molecule is capable of attaching by cohesion to all of portions (1), (2) and (3) of the sequence specific nucleic acid set molecule. The detachment or stripping away of the set molecule by the unset molecule is initiated by the cohesion of that portion of the unset molecule capable of attaching by cohesion to the toehold portion of the set molecule. A series of schematic illustrations, simplistically demonstrating how a biped (as a preferred embodiment of a multiped) with foot 1 and foot 2 can travel from one foothold to another is shown in FIGS. 1A–1G.

A given single-stranded sequence specific nucleic acid set molecule, which is referred to as a "set strand" and is shown in FIGS. 1A–1G, is designed to cohere by Watson-Crick sequence complementarity to one combination of a sequence specific nucleic acid end of a foot 10 and a sequence specific nucleic acid foothold 20, thus holding the foot and the foothold together. Each set strand also has a portion or segment (portion 3 discussed above), also known as a "toehold" (represented by the reference numeral 30), of single stranded nucleic acid which complements neither a foot nor a foothold (also known as a "dock"). This "toehold" allows the set strand to be detached or stripped away via the introduction of an appropriate single-stranded sequence specific nucleic acid unset molecule, which is referred to as an "unset strand".

Figure 1B:
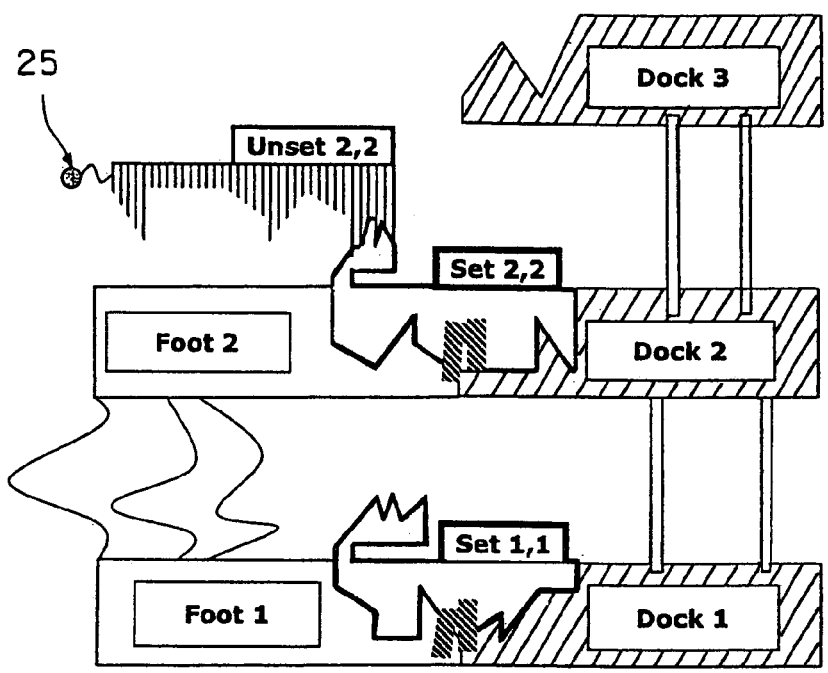
Figure 1C:
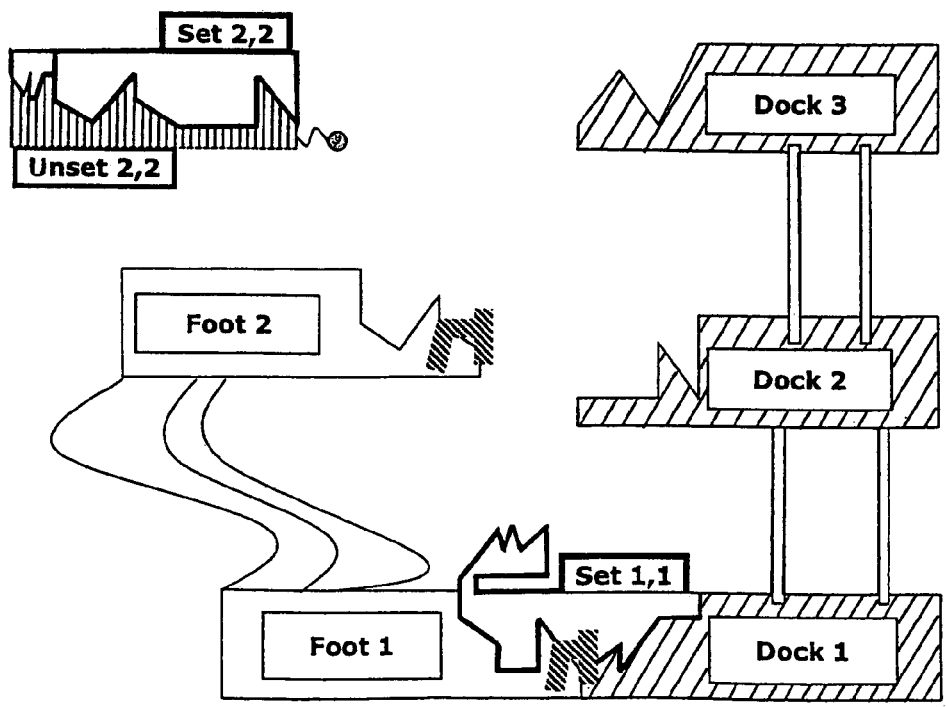
Figure 1D:
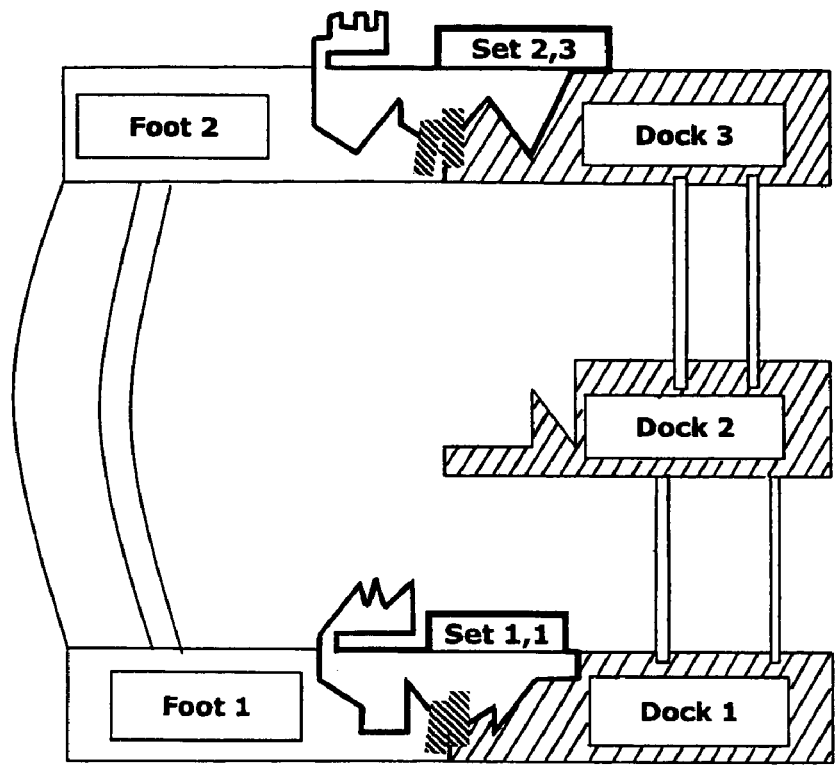
Figure 1E:
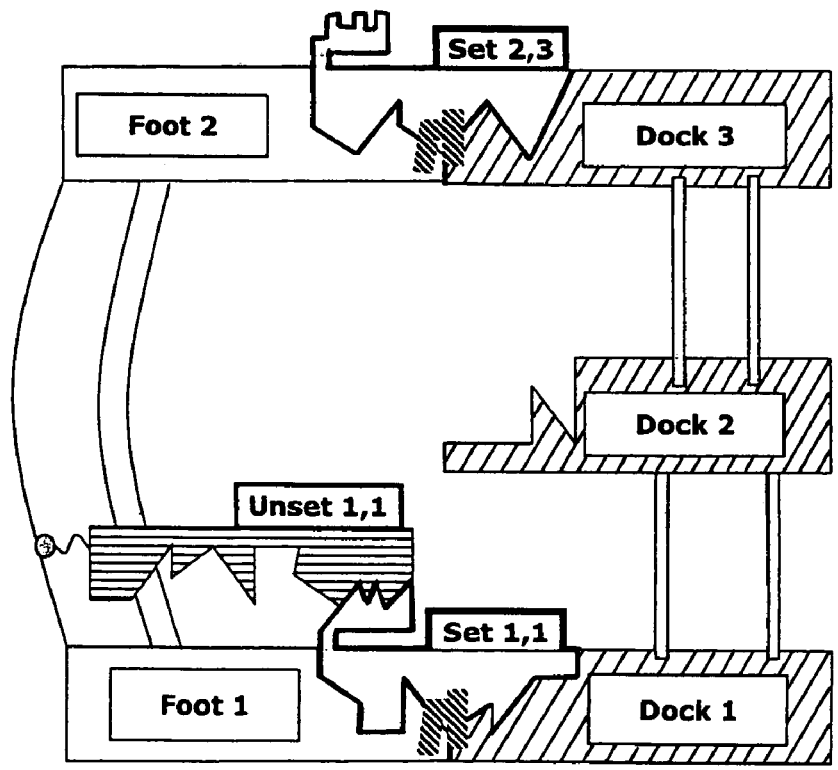
Figure 1F:
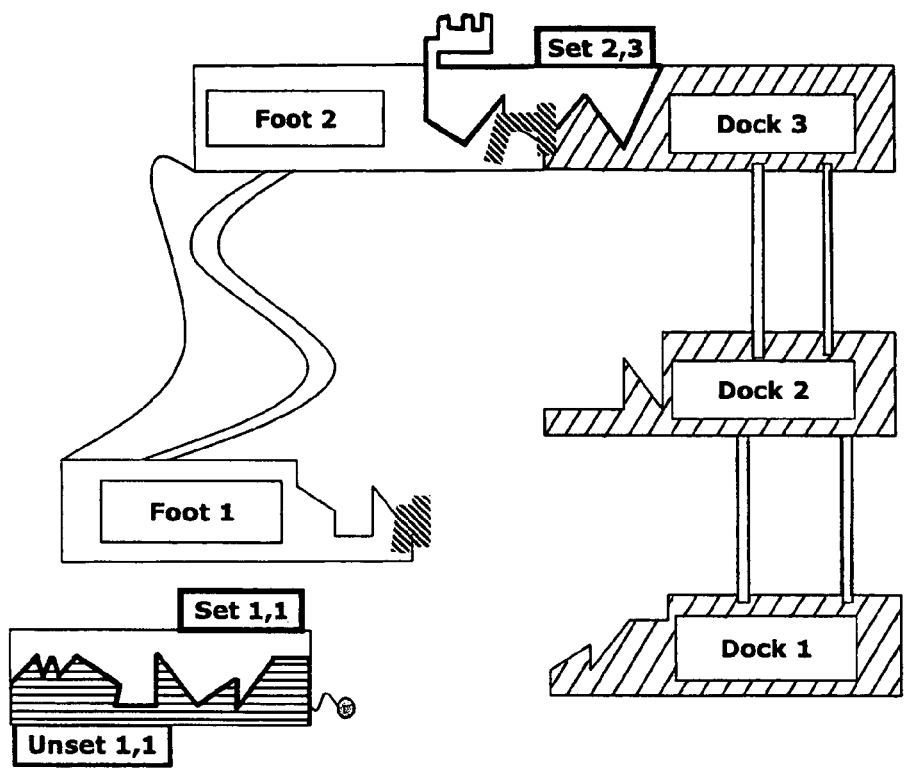
Figure 1G:
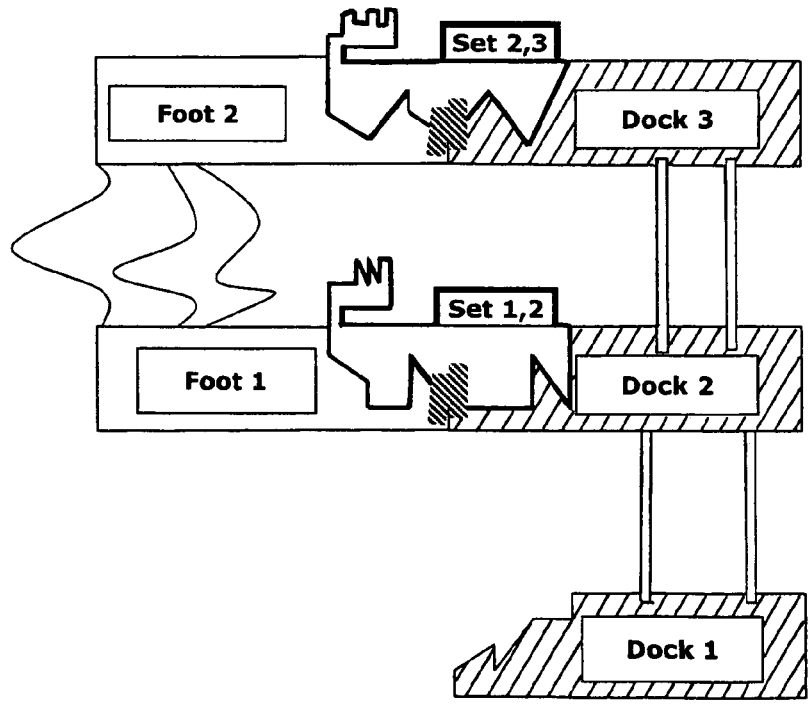

If the nano-robotic system according to the present invention starts in state 11,22 (foot 1 attached to foothold/dock 1 and foot 2 attached to foothold/dock 2) as shown in FIG. 1A, then the introduction of unset strand 22 (FIG. 1B) detaches leading foot 2 from foothold/dock 2 and leaves the system in state 11 (FIG. 1C). Subsequently, a different set strand 2,3 can be introduced to the system to attach foot 2 to foothold/dock 3 (FIG. 1D). In order for foot 2 to reach foothold/dock 3 while foot 1 is still attached to foothold/dock 1, the tether(s) between foot 1 and foot 2 must be able to accommodate the increased distance needed between foot 1 and foot 2. Trailing foot 1 takes a step from foothold/dock 1 to foothold/dock 2 in similar fashion (FIGS. 1E–1G).

Reference numeral 15 shown in FIG. 1A indicates optional psoralen molecules on the ends of the two feet of the biped, which psoralen molecules can react with neighboring bases when exposed to ultraviolet light. Thus, the psoralen molecules can be used to covalently link a foot, a set strand, and a foothold/dock and facilitate determination of where each foot is located at any given time, such as by polyacrylamide gel electrophoresis as demonstrated in Example 1 presented herein below.

Reference numeral 25 shown in FIG. 1B indicates an optional biotin molecule attached to an unset strand in the event that removal of unhybridized unset strands and/or hybridized unset/set strands from the system is desired. However, it should be noted that hybridized set and unset strands are stable and are not expected to disrupt subsequent operations.

Please note that for the series of schematic illustrations in FIGS. 1A–1G, a reference numeral is presented in the first figure in which the represented element appears.

Figure 2:
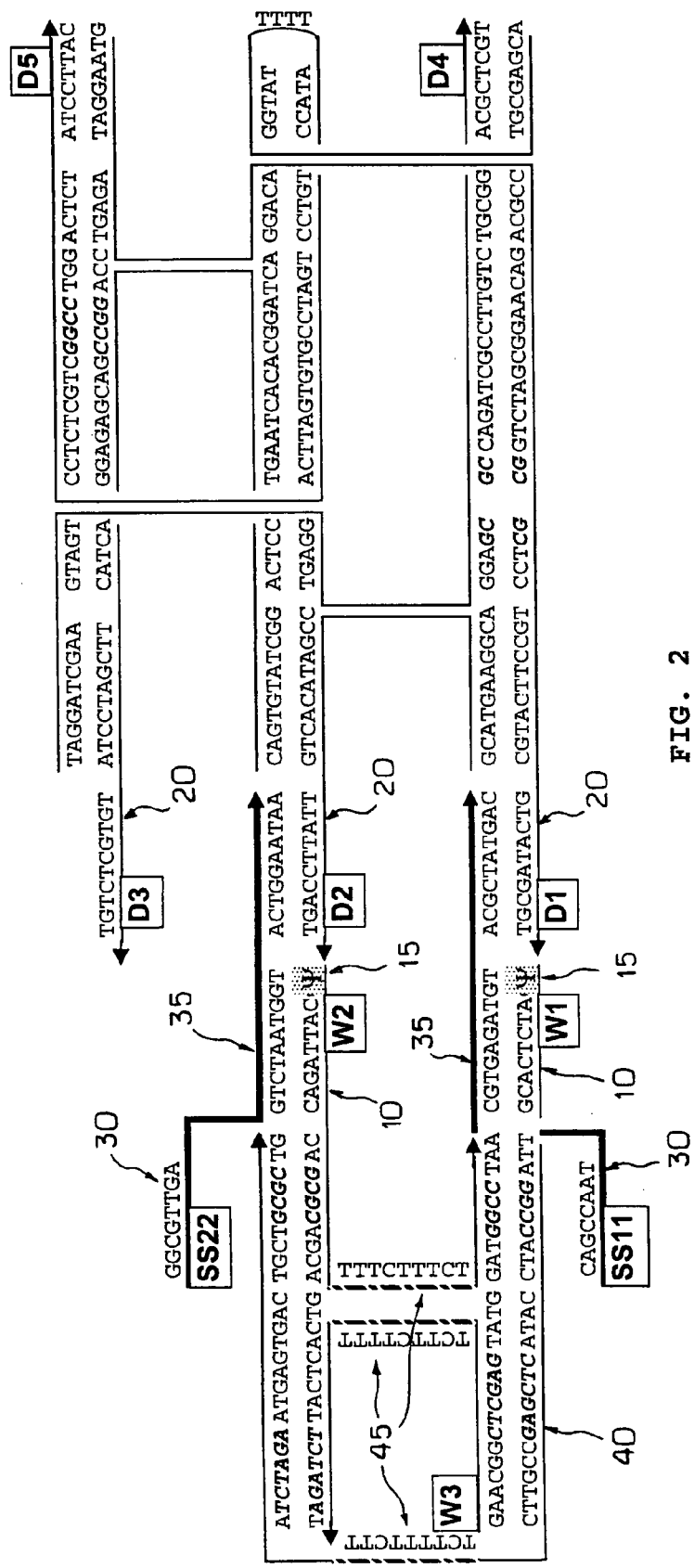
FIG. 2 shows a diagram of the strand structure of state 11, 22 as presented schematically and as generated in the Example 1 presented hereinbelow. Arrows indicate the 3' end of each strand. The sequences of the strands are as follows: W1(SEQ ID NO:1); W2(SEQ ID NO:2); W3(SEQ ID NO:3); D1(SEQ ID NO:4); D2(SEQ ID NO:5); D3(SEQ ID NO:6); D4(SEQ ID NO:7); D5(SEQ ID NO:8); SS11 (SEQ ID NO:9); and SS22(SEQ ID NO:11).

The strand structure of state 11,22, as presented schematically in FIG. 1A, is shown in FIG. 2 and is generated in Example 1 presented herein below.

Figure 3:
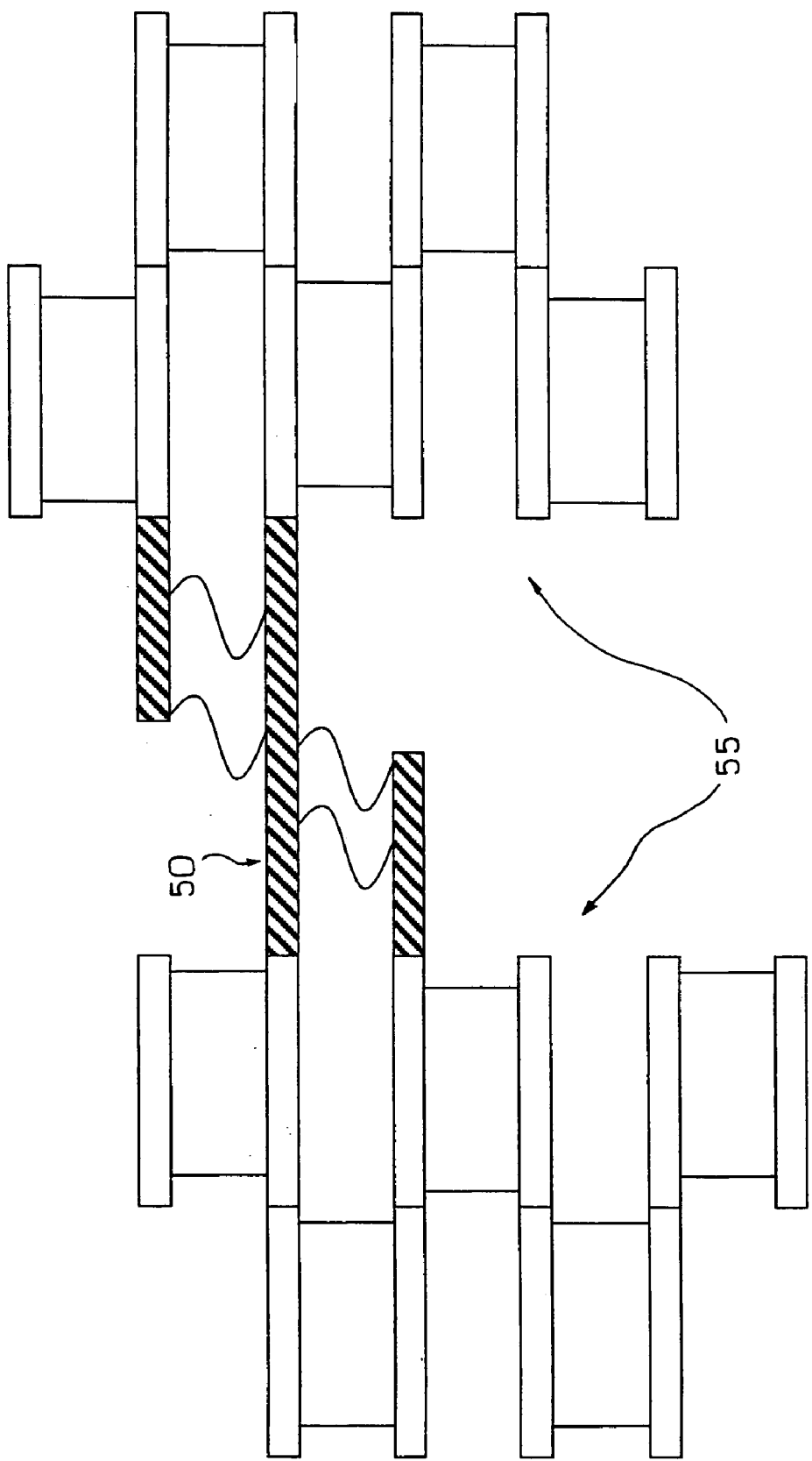
FIG. 3 shows a schematic illustration of a quadruped simultaneously traveling on two molecular paths built from linear arrays of nucleic acid double crossover molecules.

The multiped, as a component of the nano-robotic system of the present invention, is preferably a biped (i.e., having two feet), although it may have any number of feet that is two or more. For example, tripeds, quadrupeds, etc., may be used in the nano-robotic system of the present invention. However, the efficiency in which a multiped is able to travel along a molecular path may be limited as the number of feet increases because of the increased complexity and the increased number of individual steps that is needed to move the multiped as a whole. A non-limiting example of a type of quadruped 50 is shown in FIG. 3 traveling between two molecular paths 55. Another type of possible quadruped is one where all four feet of the quadruped are capable of walking together on the same path.

As will be appreciated by those of skill in the art, the multiped is capable of changing directions on the molecular path, such as reversing or backing up, or crossing over to another path when there are multiple molecular paths present in the system. This movement of the multiped relative to the molecular path is controlled by the combination of footholds located on the molecular path(s) and the sequence specific nucleic acid set molecules. With more extensive molecular paths, the multiped can walk arbitrarily far, in circles, and in two or three dimensions.

It is intended that the nano-robotic system of the present invention encompass the presence of more than one multiped on a molecular path or on multiple molecular paths. When multiple multipeds are present in the system, these multipeds may be traveling on the same path or on different paths. They may be traveling over the same region at different times or they may be stepping over or around one another on the same path. A further possibility is that there are "rest stops" designed in a molecular path which allows a multiped to "rest" while another multiped passes by along the molecular path.

Figure 4:
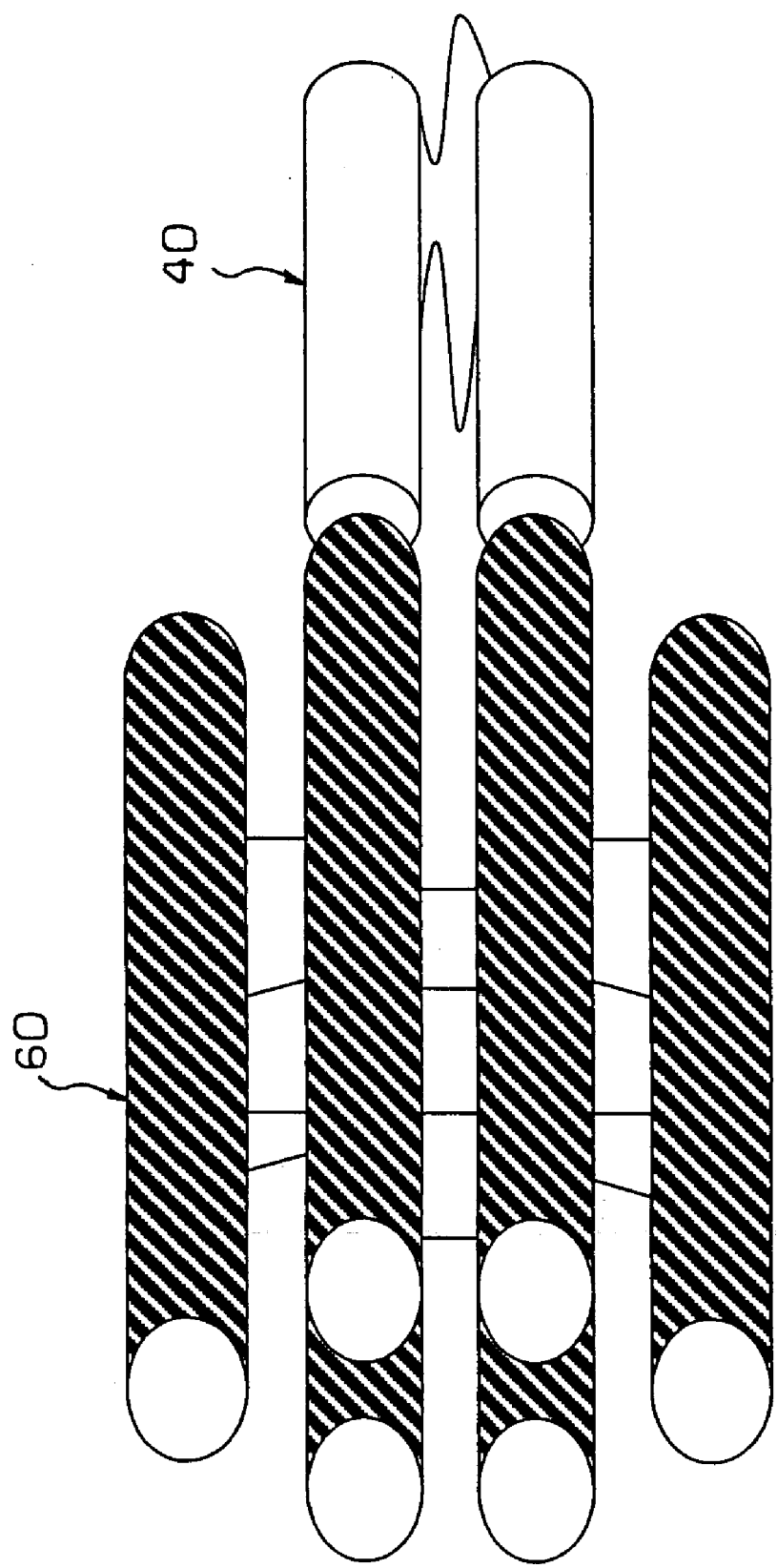
FIG. 4 shows a schematic illustration of a biped traveling around a circular bundle of six DNA helices which are laterally joined so that every adjacent pair of helices form a double crossover (DX) motif.

With regard to the molecular path, it is understood that there may be more than one molecular path that forms a plurality of molecular paths which may or may not be connected in the nano-robotic system. The molecular path or paths may be linear, such as a track, or it may be circular or in two or three dimensions. The two molecular paths 55 shown in FIG. 3 provide an example of two linear tracks. FIG. 4 provides an example of a biped 40 traveling around a circular path built from a bundle of six DNA helices 60 which are laterally joined so that every adjacent pair of helices form a double crossover (DX) motif (Mathleu et al., 2001). The travel of the biped around such a circular path effectively generates rotary motion, which finds additional utility as a nano-rotor. A molecular path preferably provides a well-defined local structure with footholds within the bounds of the range of motion of the multiped. For flexible molecular paths, it may be necessary to take extra precautions to ensure that the multiped only steps on the desired footholds. For instance, the path might be a covered path, like a tunnel, so that a multiped on the path would only have access to nearby footholds.

Figure 5:
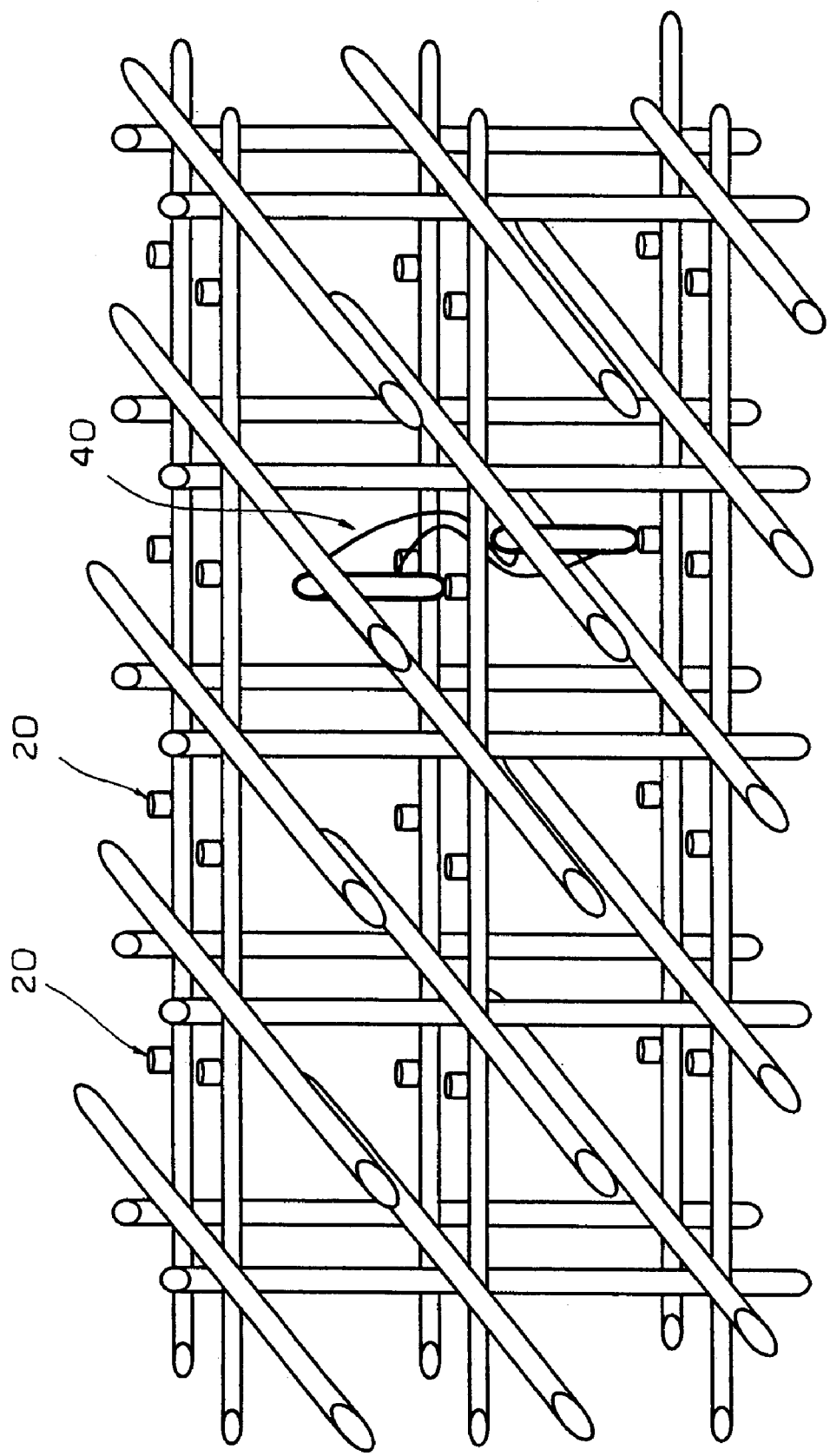
FIG. 5 shows a schematic illustration of a biped traveling through a three dimensional lattice and stepping from one plane to another.

Non-limiting examples of two and three dimensional arrays suitable as a two or three dimension network of molecular paths are provided in Liu et al. (1999), LaBean et al. (2000), and U.S. Pat. No. 6,255,469, the entire contents of which are incorporated herein by reference. The arrays in the above cited references are composed of double (i.e., DAO and DAE), triple, or multi-crossover nucleic acid molecules with bulged junctions providing hairpins that stick out of a plane of the array. The multiped in the nano-robotic system of the invention may use these hairpins as the footholds of the path along which it travels. FIG. 5 shows a biped 40 traveling through a three dimensional lattice (array) with regularly spaced footholds 20 (shown as short vertical struts). It is intended that the arrays can be a mixture of multicrossover nucleic acid molecules such as double (DAO, DAE) and triple (TX) cross-over nucleic acid molecules.

Figure 6A:
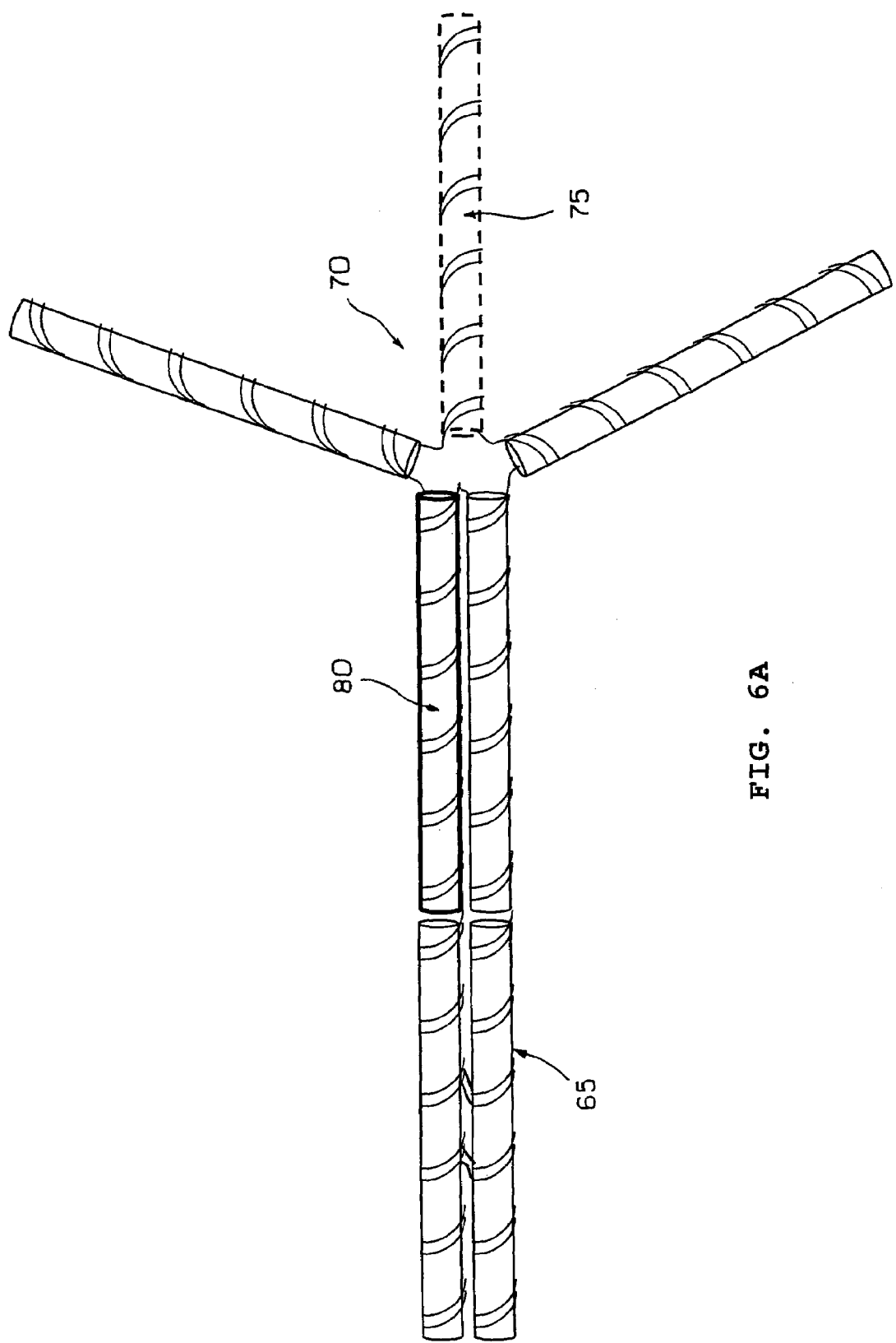
FIGS. 6A and 6B show schematic illustrations of a minimally flexible biped controlling the structure of a flexible molecular path composed of a five arm junction.
Figure 6B:
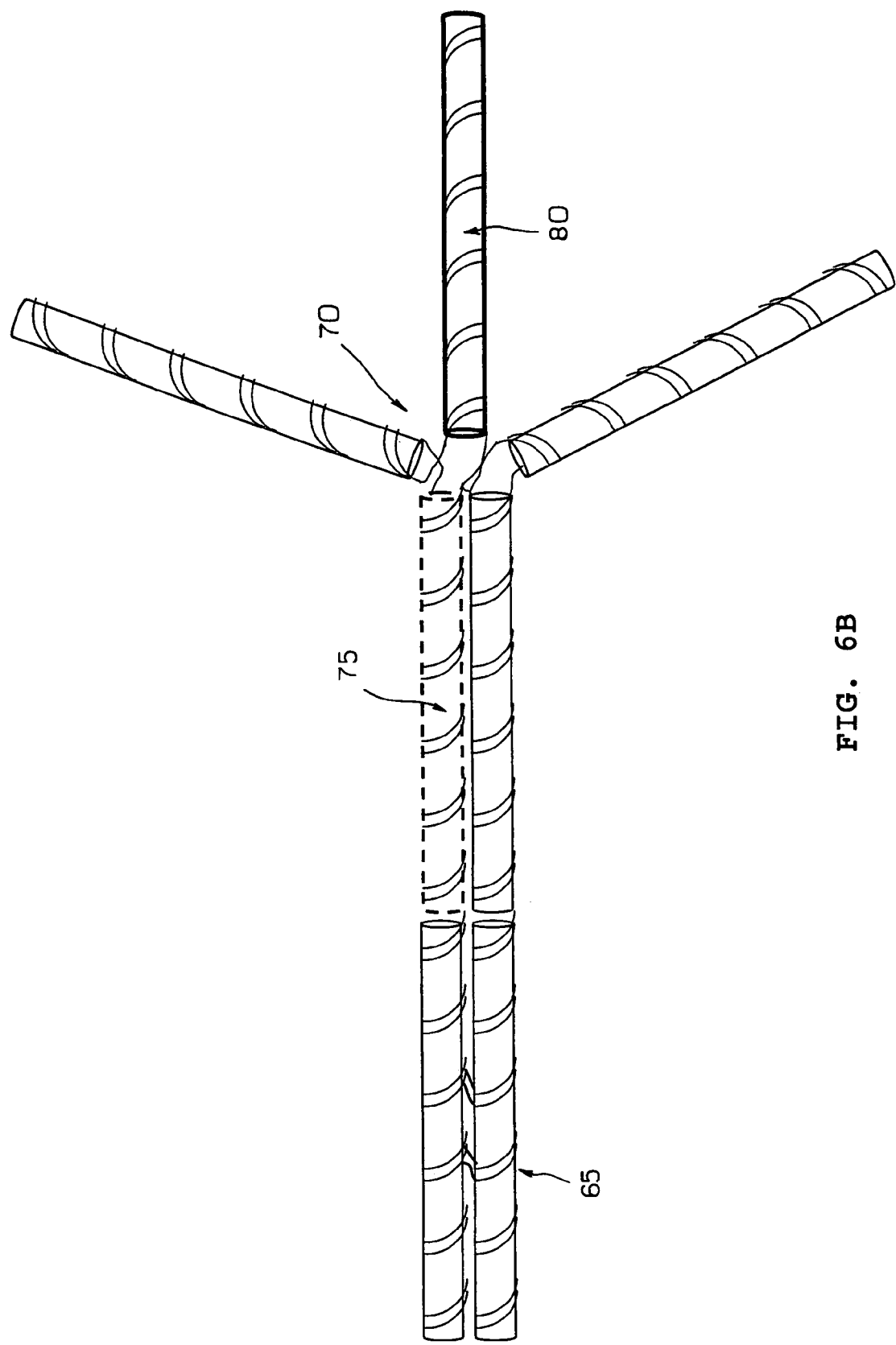

As a further embodiment of the molecular path, the molecular path can be a flexible path. For example, FIGS. 6A–6B show a minimally flexible biped 65 (tethers are short and hold the two feet closely together) which can be used to control the structure of a five arm junction as a flexible path 70. Two arms can be positioned next to each other by attaching the foothold on each arm to one of the two feet on the biped. In FIG. 6A, the dashed arm 75 is shown floating free while the thick line arm 80 is shown to be held in place by the biped. FIG. 6B shows that the thick line arm 80 has been released from the biped and the dashed arm 75 is attached to the biped in its place.

The term "nucleic acid" as used herein is any polymeric system containing a sequence of two or more monomers (henceforth referred to as "nucleotides") where individual nucleotides are capable of forming highly specific paired interaction with other nucleotides, i.e., they form weak bonds with some nucleotides, vanishingly weak bonds with others, or they may even repel some other nucleotides. The interactions or bonds between nucleotides must be weak enough to be broken individually but strong enough that the cooperative action of a few neighbors forms a stable hybrid. A feature of the nucleotides is that they are capable of interacting with a nucleotide opposing them to form a specifically paired attraction. In natural DNA and RNA, hydrogen bonding forms this interaction. Non-limiting examples of nucleic acids include DNA, RNA, Peptide Nucleic Acid (PNA), and Locked Nucleic Action (LNA). A review of some nucleic acid variations, including derivatized/modified bases and other unusual bases, is presented in Freier et al. (1997). Hunter et al. (2003) recently reported the development of a synthetic nucleic acid which is composed of elements completely different from DNA.

In the nano-robotic system according to the present invention, the advantageous property of sequence specific interaction is found in the nucleic acid ends of the feet of the multiped, in the nucleic acid footholds of the molecular path and in the nucleic acid set and unset molecules. These nucleic acids may be single stranded or double stranded and may form 3, 4 or more stranded structures. FIG. 2 presents an example where the nucleic acid feet, footholds/docks, and set molecules are all single stranded and the attachment of a foot to a foothold is by way of sequence specific cohesion, in the form of Watson-Crick sequence complementarity, to a set strand. A single stranded unset molecule is then used to release the set strand from its interaction with a foot and a foothold.

Figure 7:
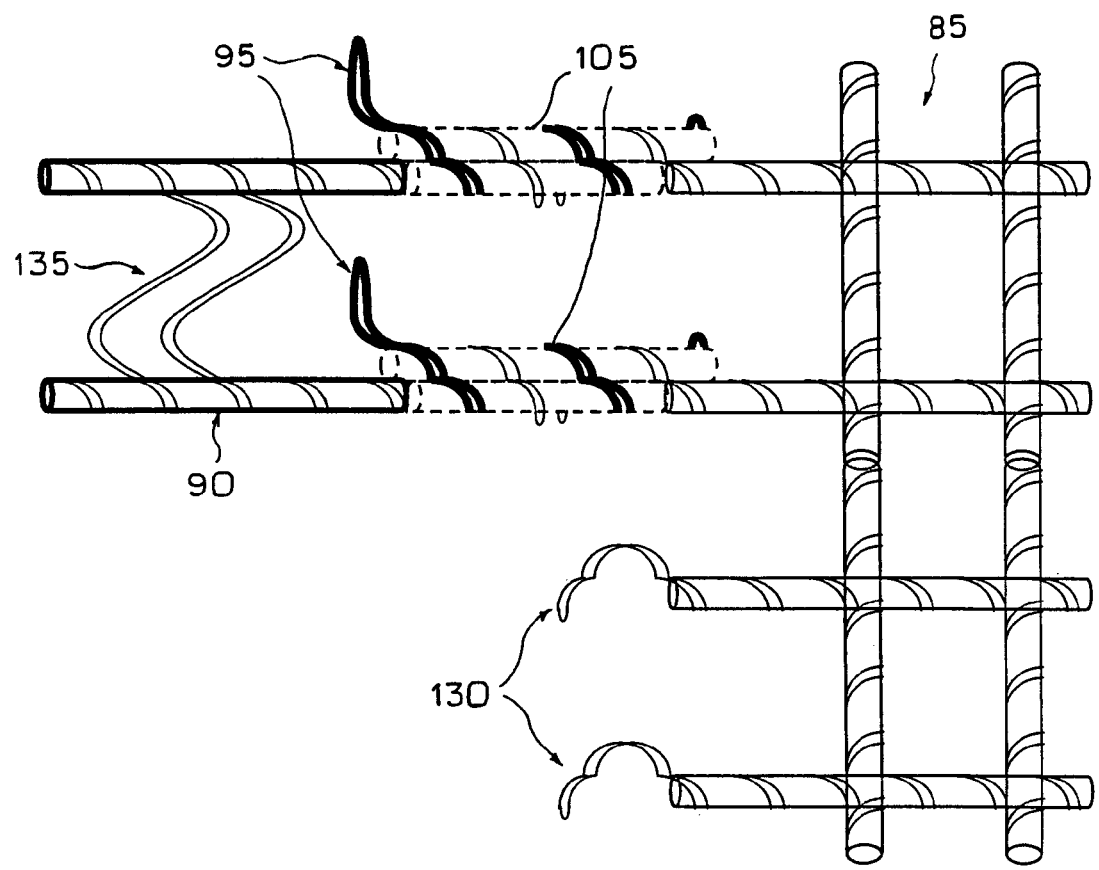
FIG. 7 shows a schematic illustration of a biped attached to footholds on a molecular path by means of paranemic cohesion to a double stranded set molecule.
Figure 8:
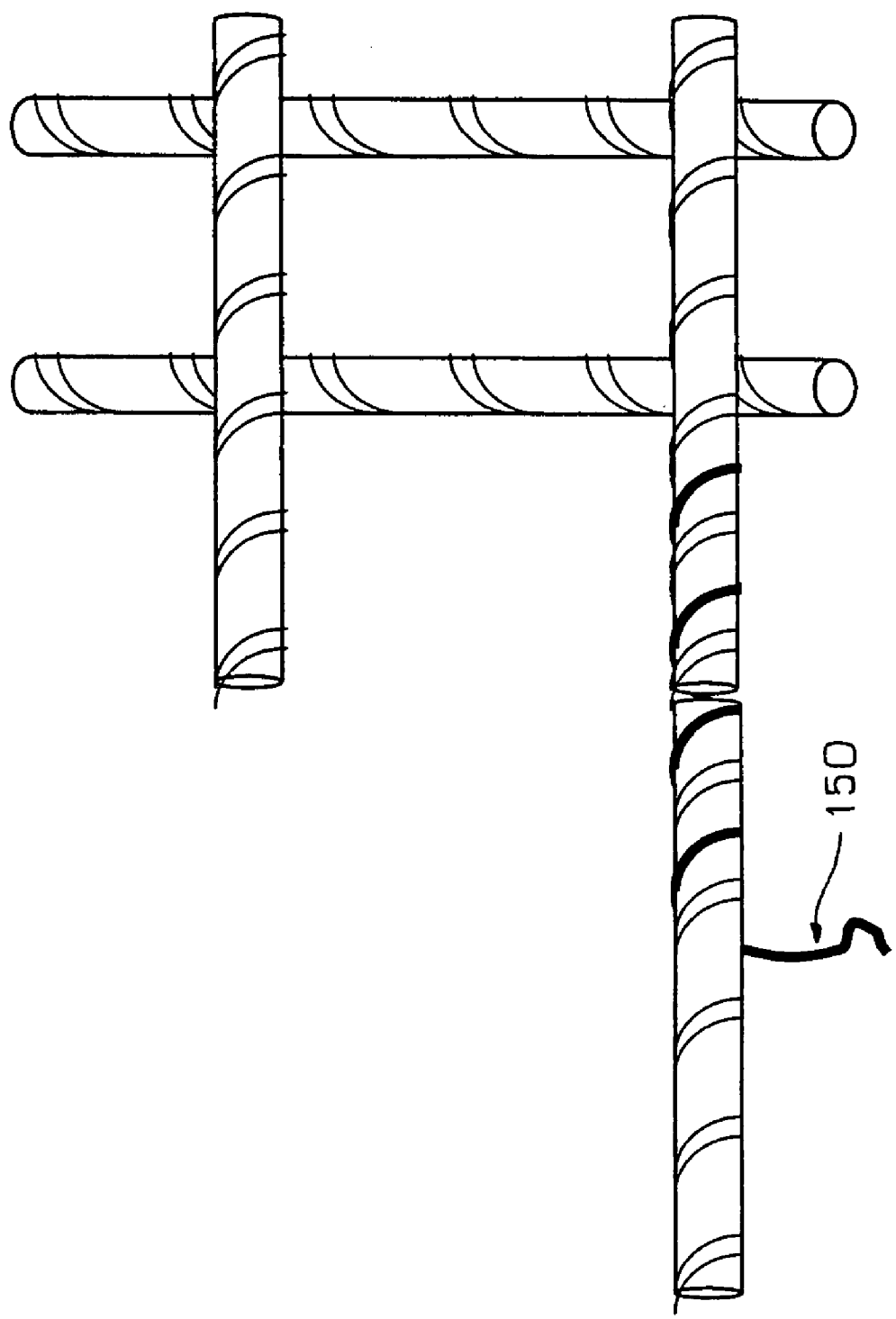
FIG. 8 shows a schematic illustration of triplex cohesion of a single stranded set molecule to a double stranded foot and to a double stranded foothold.

Alternatively, interaction between two double stranded molecules or between a single stranded molecule and a double stranded molecule can provide the sequence specific cohesion necessary for attachment of a foot of a multiped to a foothold. FIG. 7 illustrates paranemic cohesion, a form of interaction between two double stranded molecules. A double stranded set molecule 105 with toehold 95 attaches the double stranded feet of biped 90 to the double stranded footholds 130 of molecular path 85 by paranemic cohesion. See Zhang et al. (2002) and Yan et al. (2002) for disclosures of paranemic cohesion and paranemic crossover (PX) molecules. A variation on paranemic cohesion is tecto RNA, which involves oscillating loops in RNA (Jaeger et al., 2001). FIG. 8 provides an example of a cohesive interaction between a single stranded molecule and a double stranded molecule, where stretches of DNA containing purine repeats on one strand and pyrimidine repeats on the other strand can form triplex DNA. The third strand of DNA acts as the set strand for the triplex 150. A single stranded unset molecule is then used to detach the set strand, analogous to what is shown in FIGS. 1A–1G. There are many kinds of triplex interactions well known in the art. Some reviews of such interactions are found in Frank-Kamenetski et al. (1995) and Chan et al. (1997).

Figure 9A:
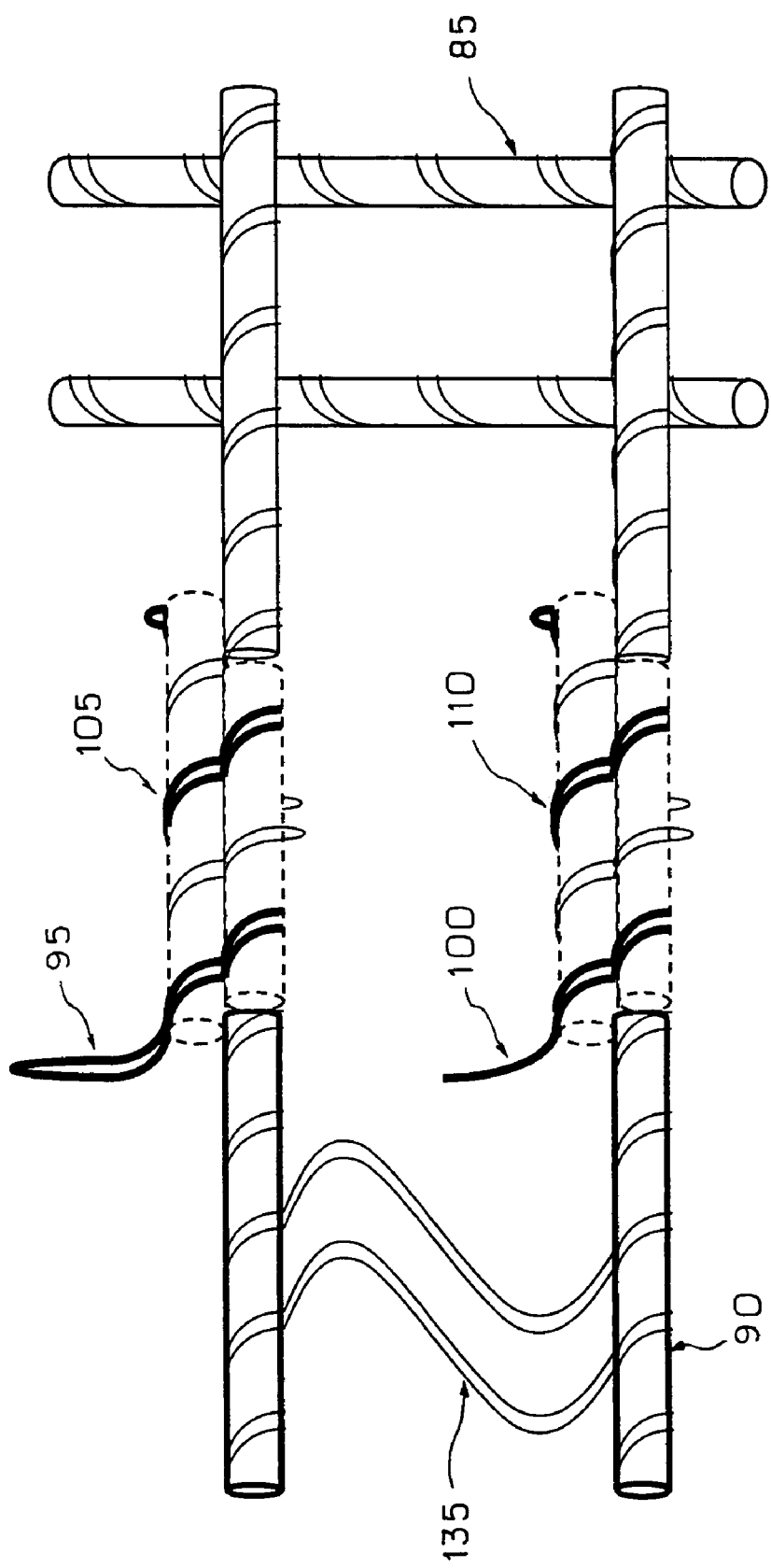
Figure 9B:
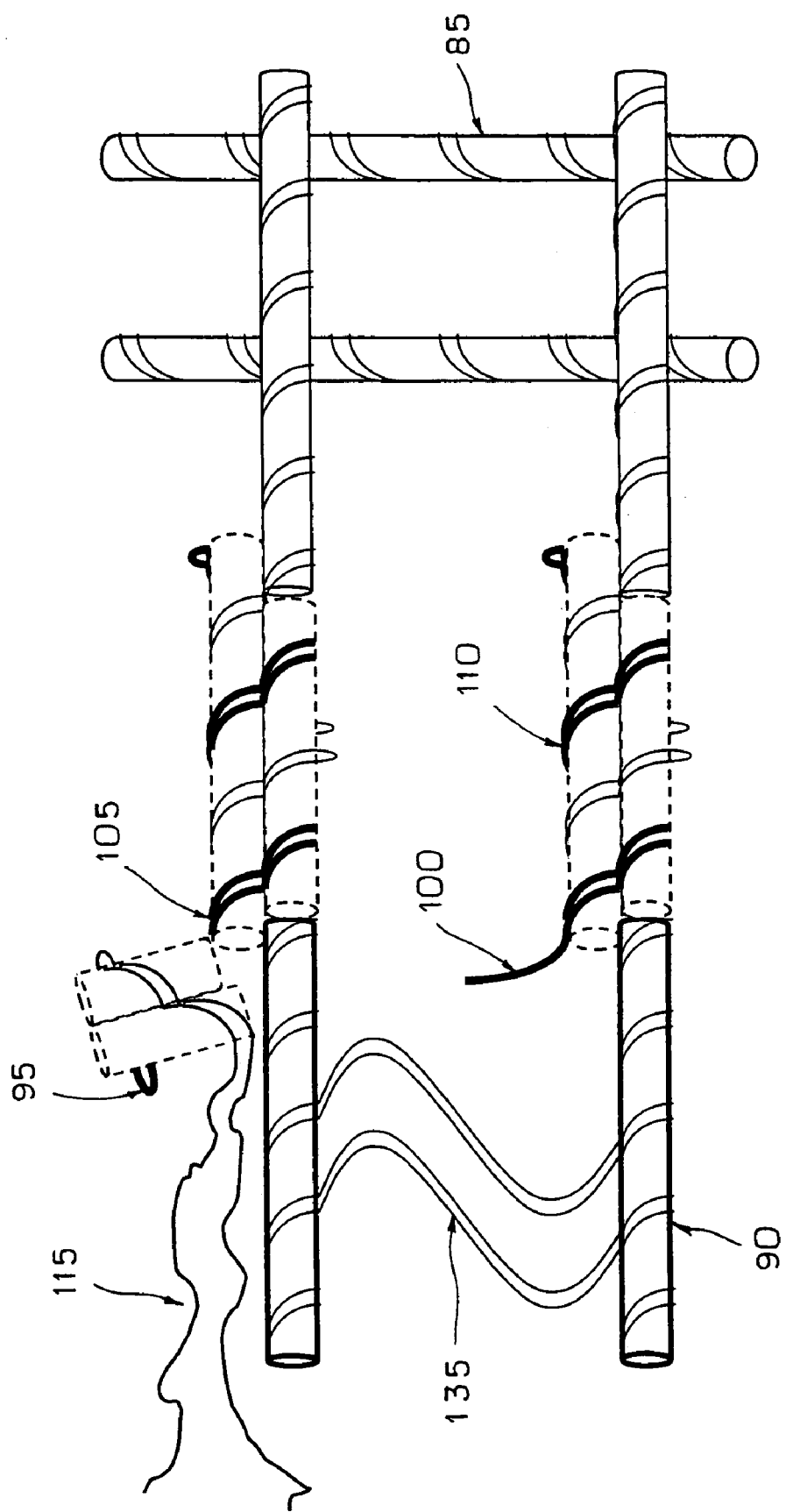
Figure 9C:
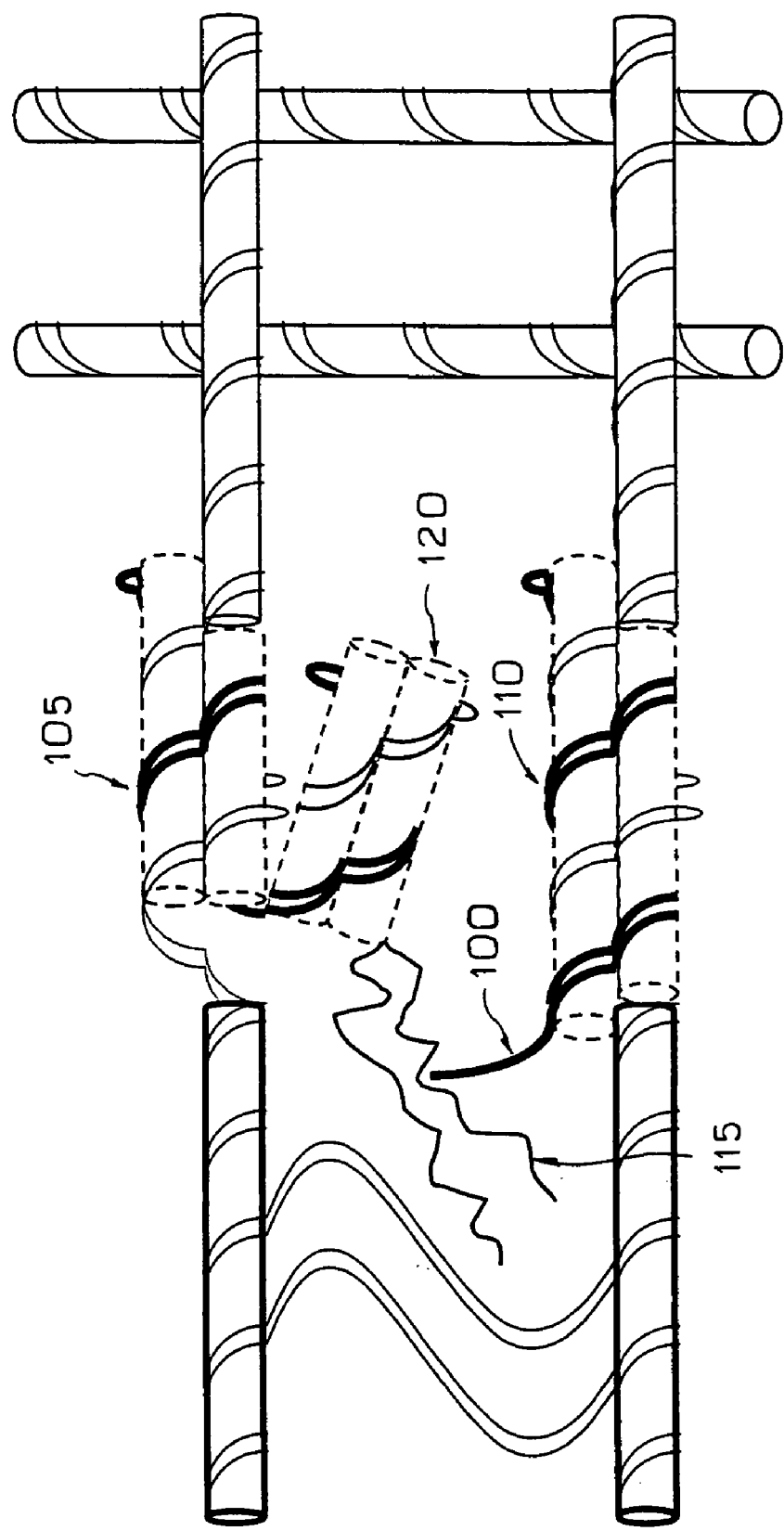
Figure 9D:
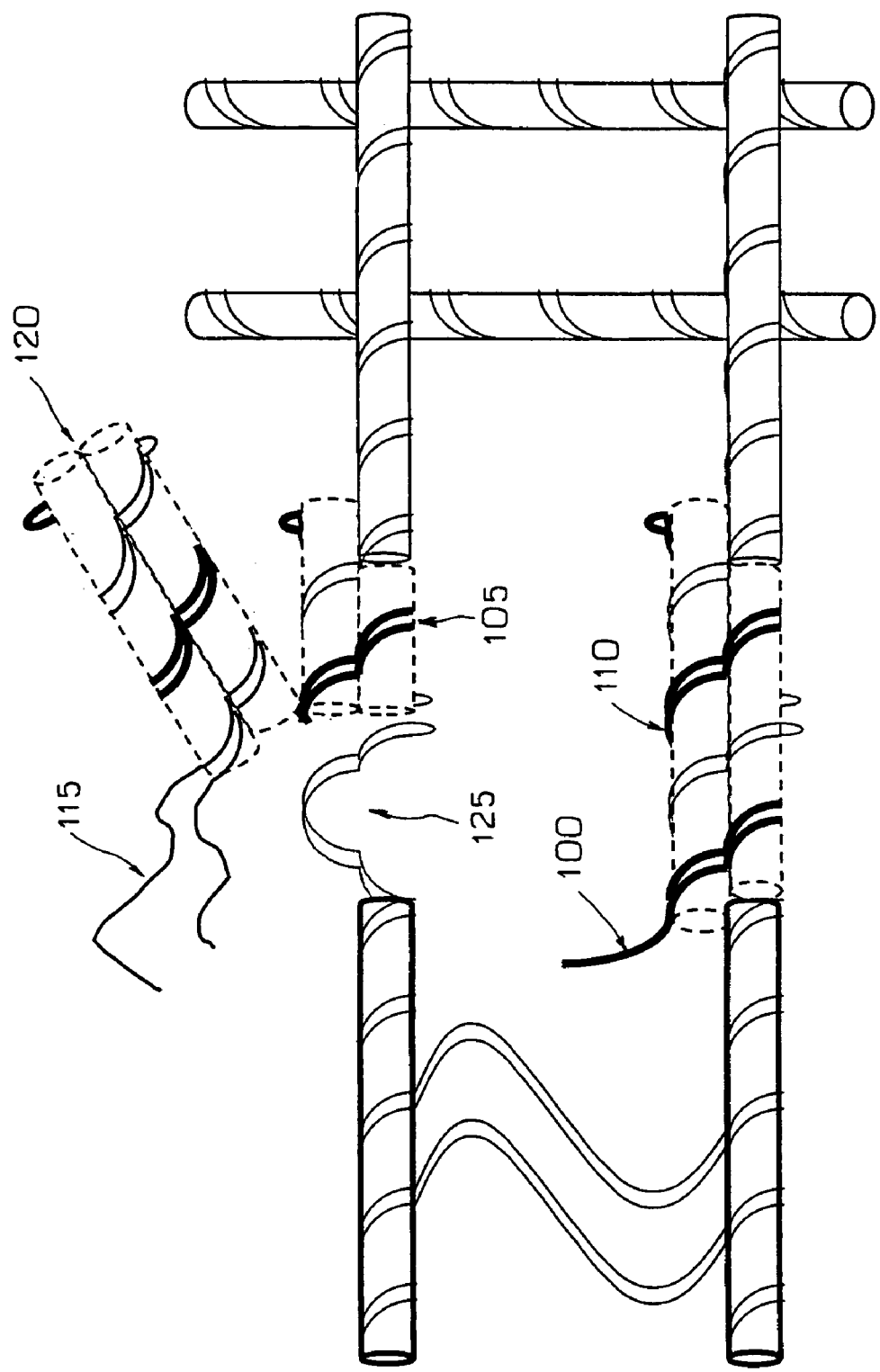
Figure 9E:
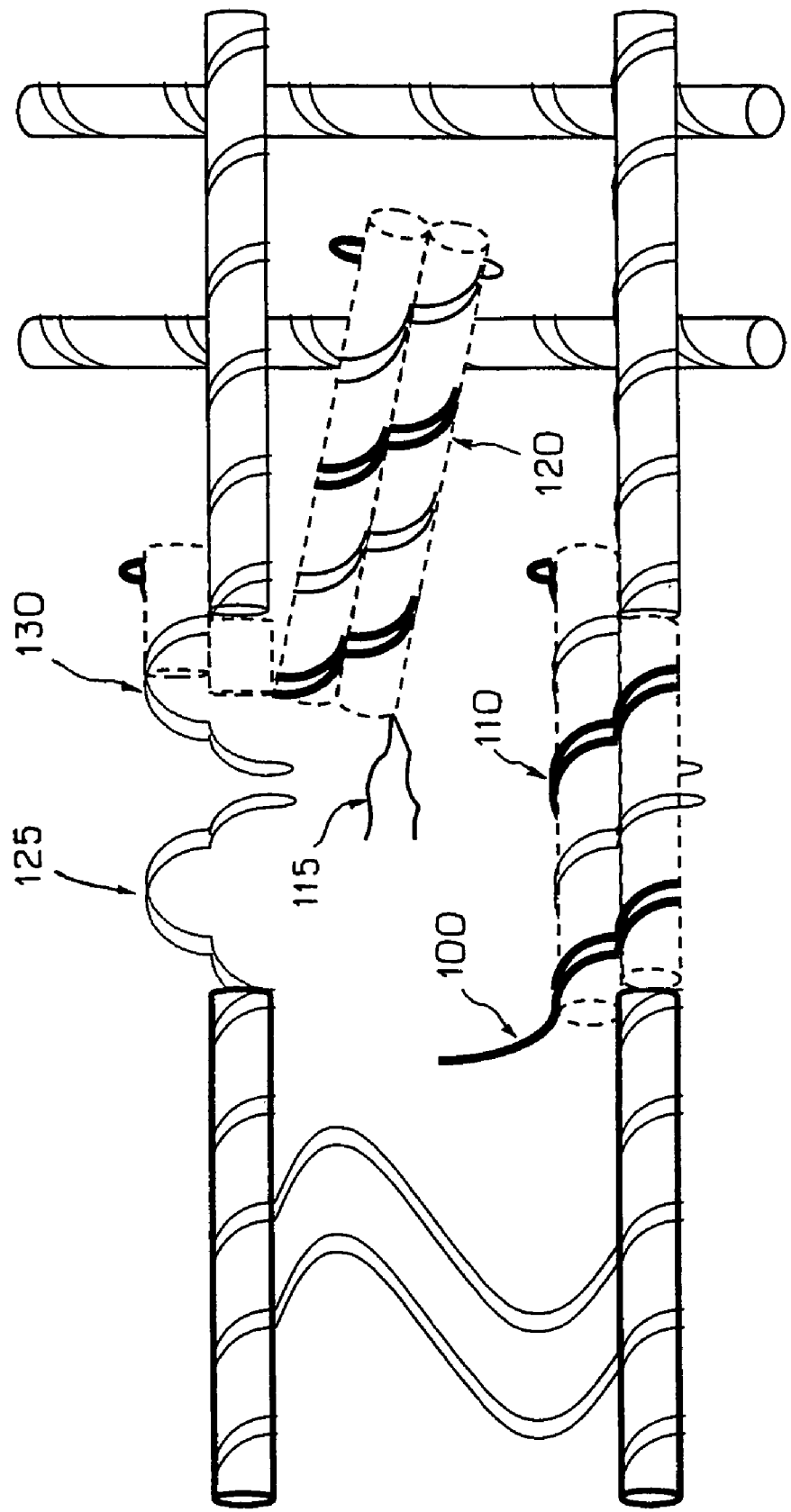
Figure 9F:
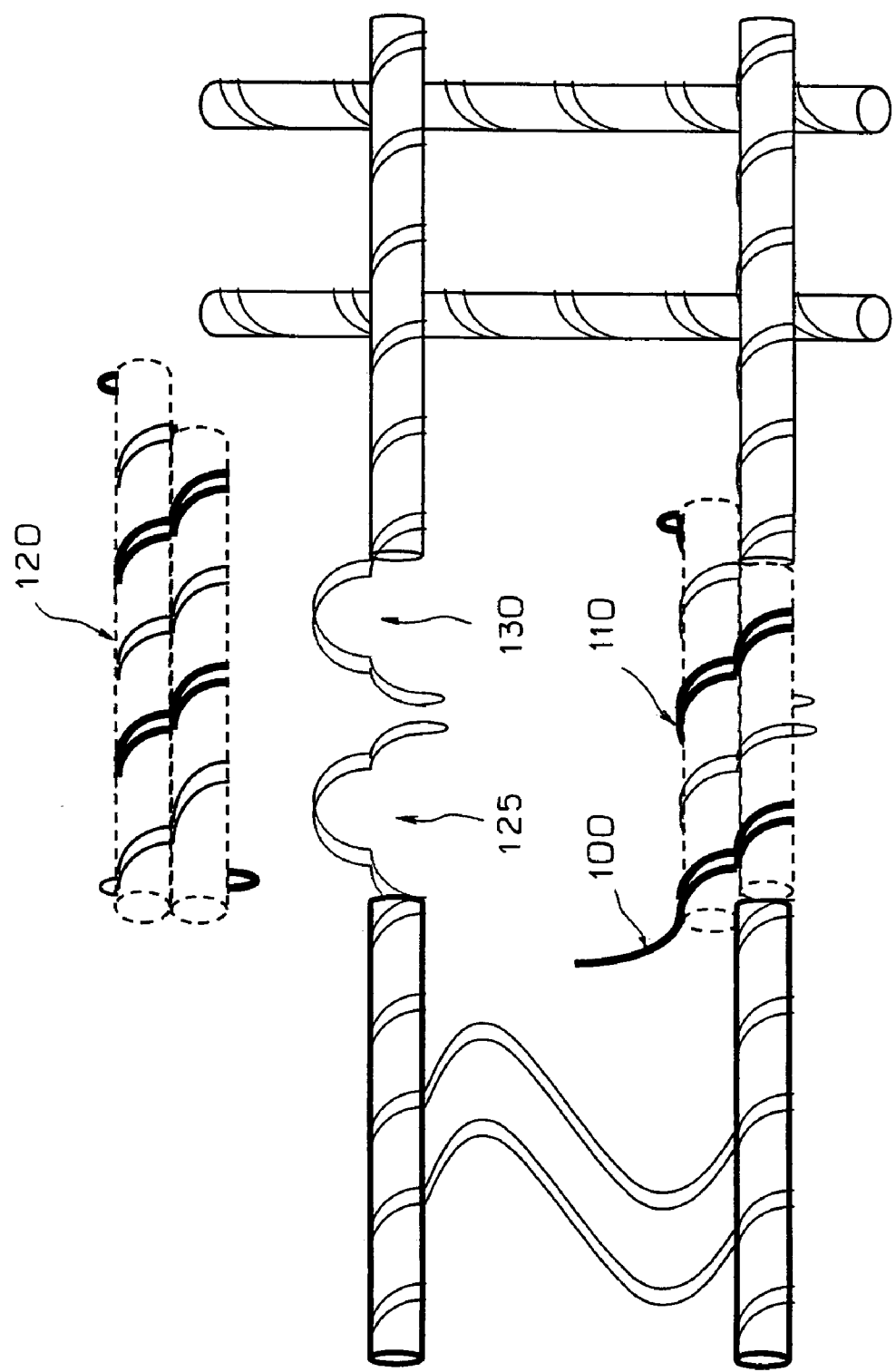

With regard to how a double stranded set molecule is detached from a state of paranemic cohesion to a foot of a multiped and a foothold of a molecular path in order to release the foot from the foothold, FIGS. 9A–9K present schematic illustrations of how such a detachment occurs. Two set molecules 105 and 110 (thick black lines) are each shown in FIG. 9A to be in paranemic cohesion with a foot of biped 90 and a foothold of molecular path 85. The two feet of the biped are tethered together by tethers 135. The upper set molecule 105 in FIG. 9A, which has a double stranded toehold 95, is a dumbbell (circular strand of nucleic acid), whereas the lower set molecule 110, which has a single stranded toehold 100, is a linear strand. Removal of set molecule 105 via a paranemic crossover (PX) structure is initiated by the formation of a PX domain between unset molecule 115 and set molecule 105 at toehold 95 (FIG. 9B). In FIG. 9C, the set 105 and unset 115 molecules extend their PX domain 120 via a stochastic process analogous to conventional branch migration. The newly formed PX domain winds around as the migration proceeds and releases a foot from a foothold (FIGS. 9D and 9E). FIG. 9F shows the upper foot 125 released from the foothold 130 with the set molecule fully detached and in paranemic cohesion with the unset molecule as paranemic structure 120.

Figure 9G:
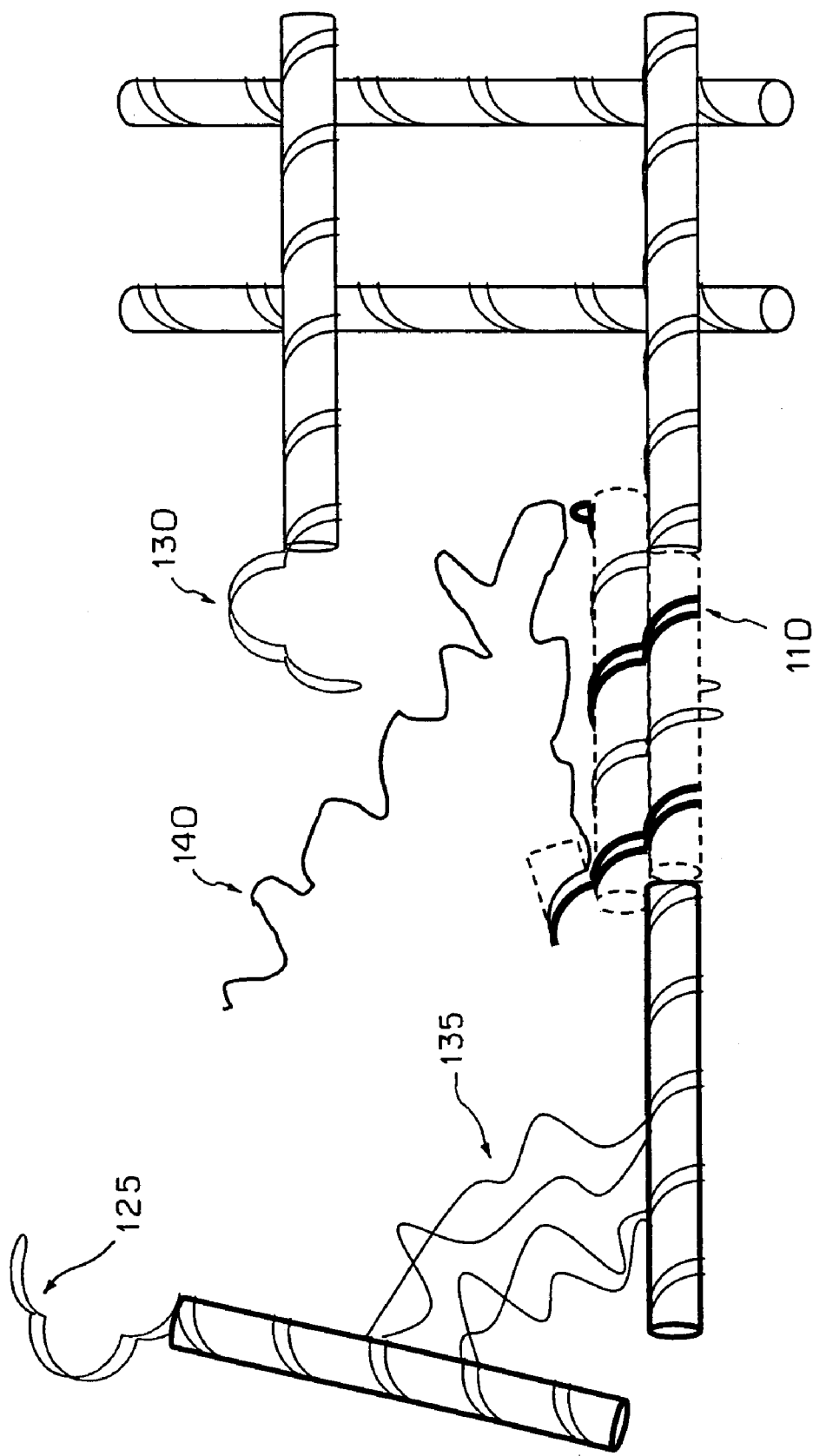
Figure 9H:
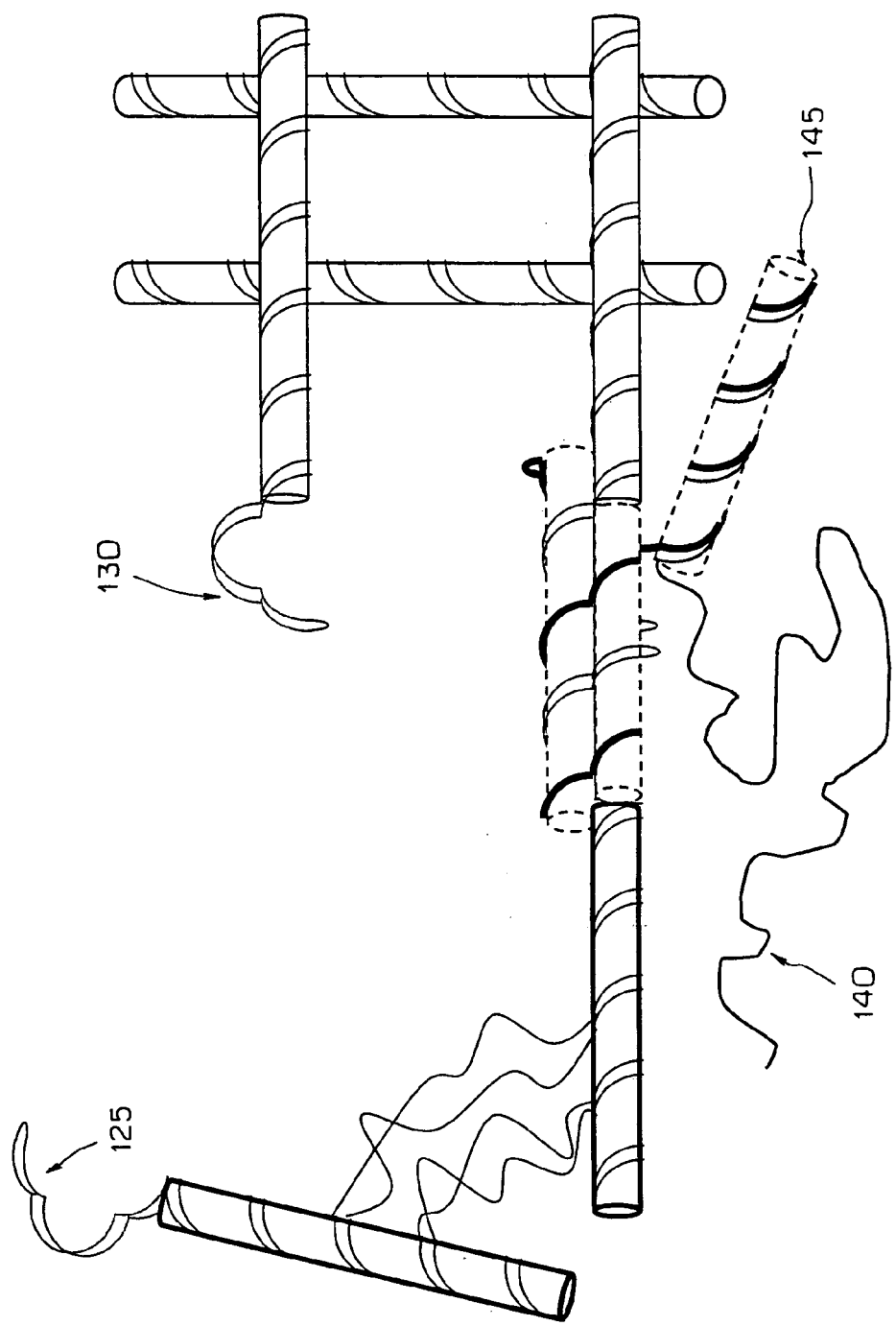
Figure 9I:
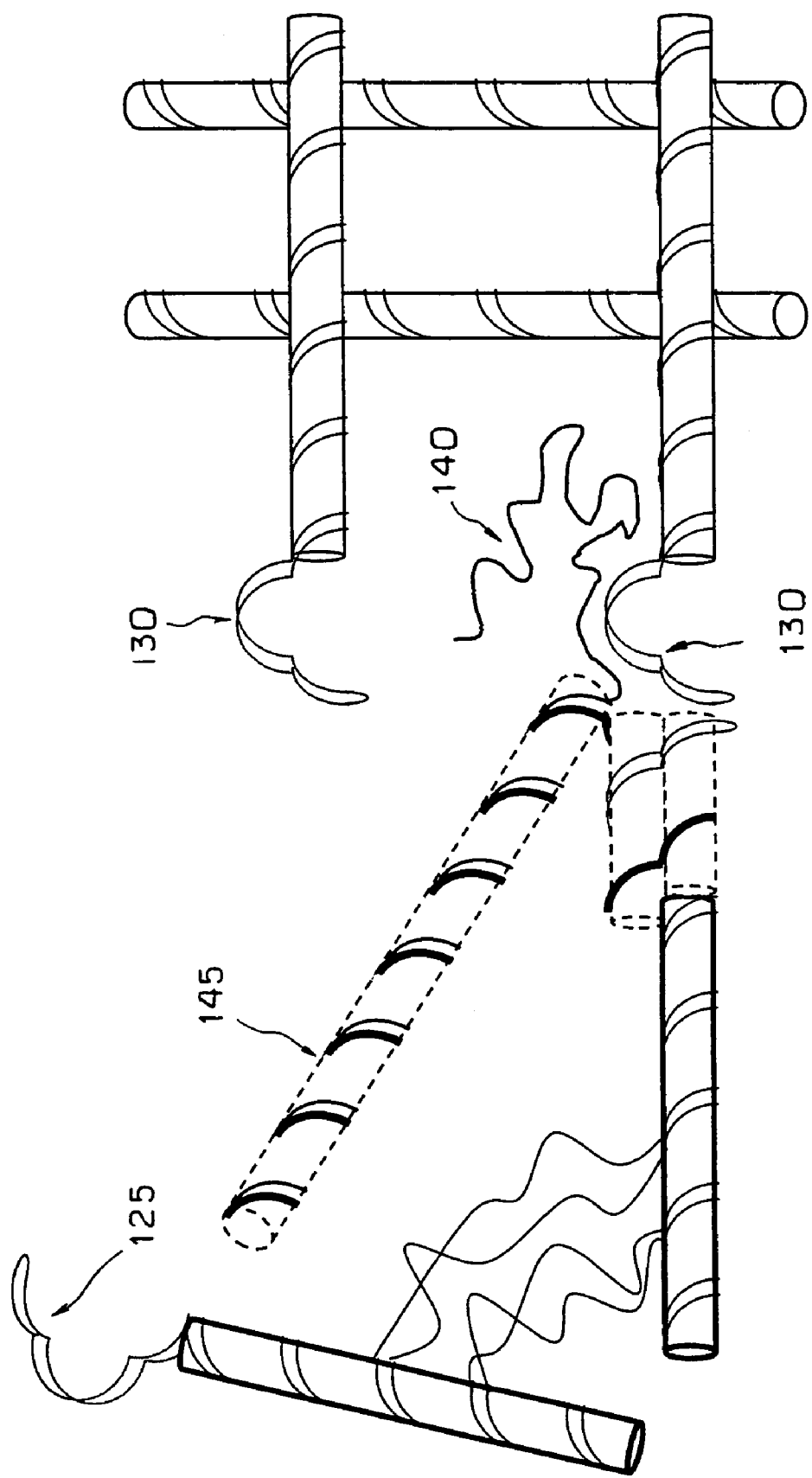
Figure 9J:
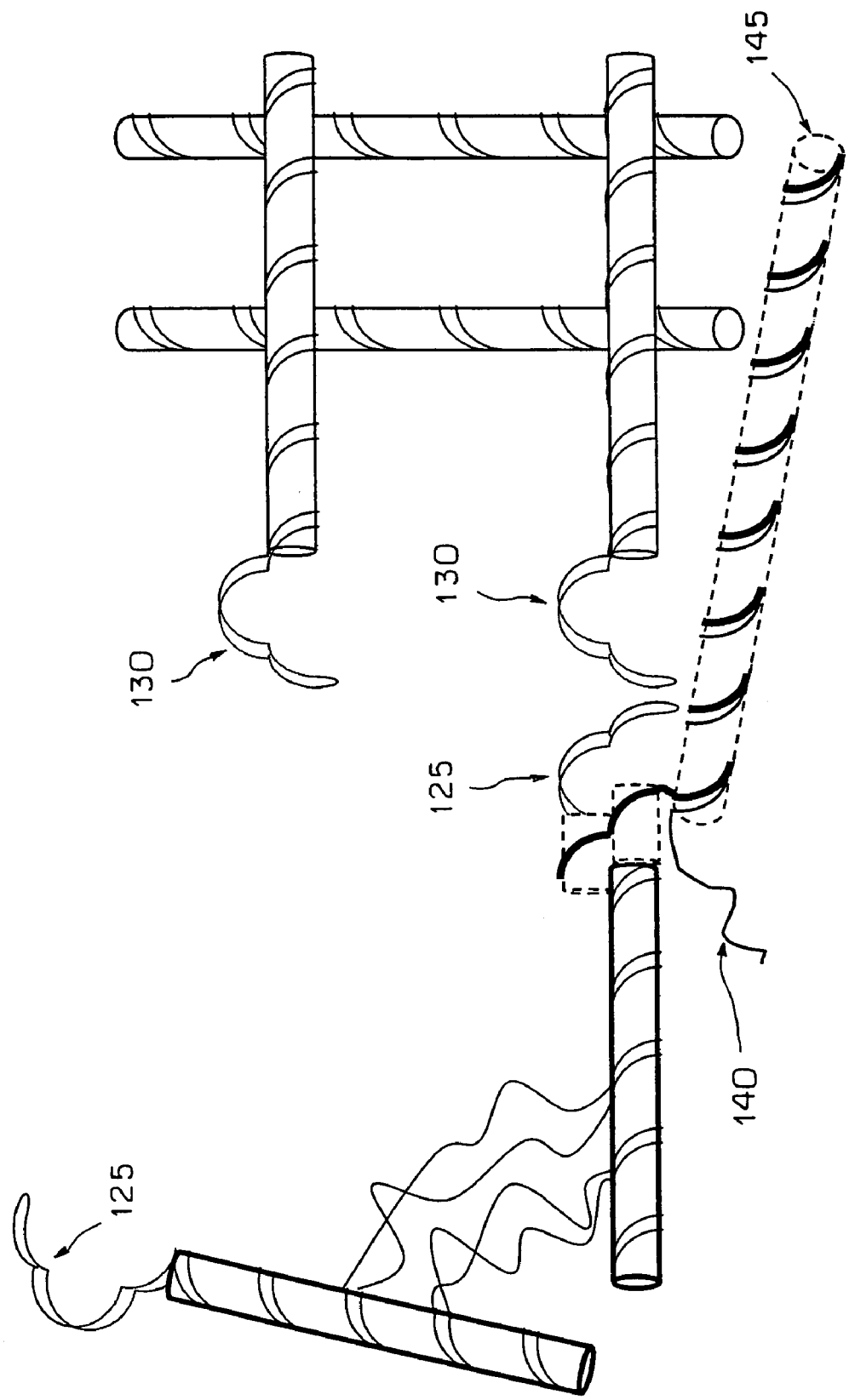

In FIG. 9G, a single stranded unset molecule 140 initiates release of the lower foot from its foothold by forming a hybrid (double strand) with the single stranded toehold of set molecule 110. Conventional branch migration proceeds to remove the set molecule in FIG. 9H. FIGS. 9I and 9J show further sequential branch migration forming a duplex 145 (double strand) and releasing the lower foot 125 from the lower foothold 130. Finally, the set molecule is fully detached from the lower foot and foothold and forms a duplex 145 with the unset molecule (FIG. 9K).

As can be seen from FIGS. 9A–9K, single stranded or double stranded toeholds can be used to detach or strip away the set molecule by initiating cohesion of the unset molecule with the toehold. Thus, the removal of a set molecule occurs when an unset molecule, designed to cohere to the set molecule, is introduced and binds to the toehold of the set molecule by cohesion, e.g., paranemic cohesion or hybridization in the form of Watson-Crick sequence complementarity. The unset molecule then proceeds to bind to the rest of the set molecule via branch migration to release a foot from a foothold. This transition from the attachment of a foot with a foothold by a set molecule to the release of the foot from the foothold is highly entropically favored because it creates disorder and is also enthalpically favored because more specific interactions, i.e., base pairs, are formed between the set and unset molecules than between the set molecule and a foot and foothold. The toehold for binding to an unset molecule by cohesion should be of sufficient length to allow the unset molecule to firmly bind before branch migration is able to proceed to displace the set molecule from its cohesion to a foot and foothold. Accordingly, a toehold of one or two nucleotides or pairs of nucleotides (also referred to herein as bases or base pairs) is not expected to be enough. Preferably, the length of the toehold is in the range of about five to fifteen bases or base pairs.

The present invention is also directed to a method for positioning a foot of the multiped of the nano-robotic system from one foothold to another along the molecular path. This method involves adding a sequence specific nucleic acid unset molecule to release a foot of a multiped off a first sequence specific nucleic acid foothold on a molecular path by stripping away a sequence specific nucleic acid set molecule which is attached by cohesion to both a sequence specific nucleic acid end of a foot of the multiped and the first sequence specific nucleic acid foothold. The added sequence specific nucleic acid unset molecule initially binds to the toehold of the sequence specific nucleic acid set molecule by cohesion before stripping away the sequence specific nucleic acid set molecule. To complete a step of the foot onto another (second) sequence specific nucleic acid foothold on the molecular path, a different sequence specific nucleic acid set molecule is added. This added set molecule permits the docking/attachment of the foot to the second foothold by cohesion with both the sequence specific nucleic acid end of the foot and the second sequence specific nucleic acid foothold.

In the event that for some reason the sequences of the footholds repeat frequently in the molecular path or in the network of molecular paths, there may be cross-talk if two feet are both supposed to be standing on footholds with identical sequences. This situation can be avoided by designing more footholds with different sequences.

Figure 10:
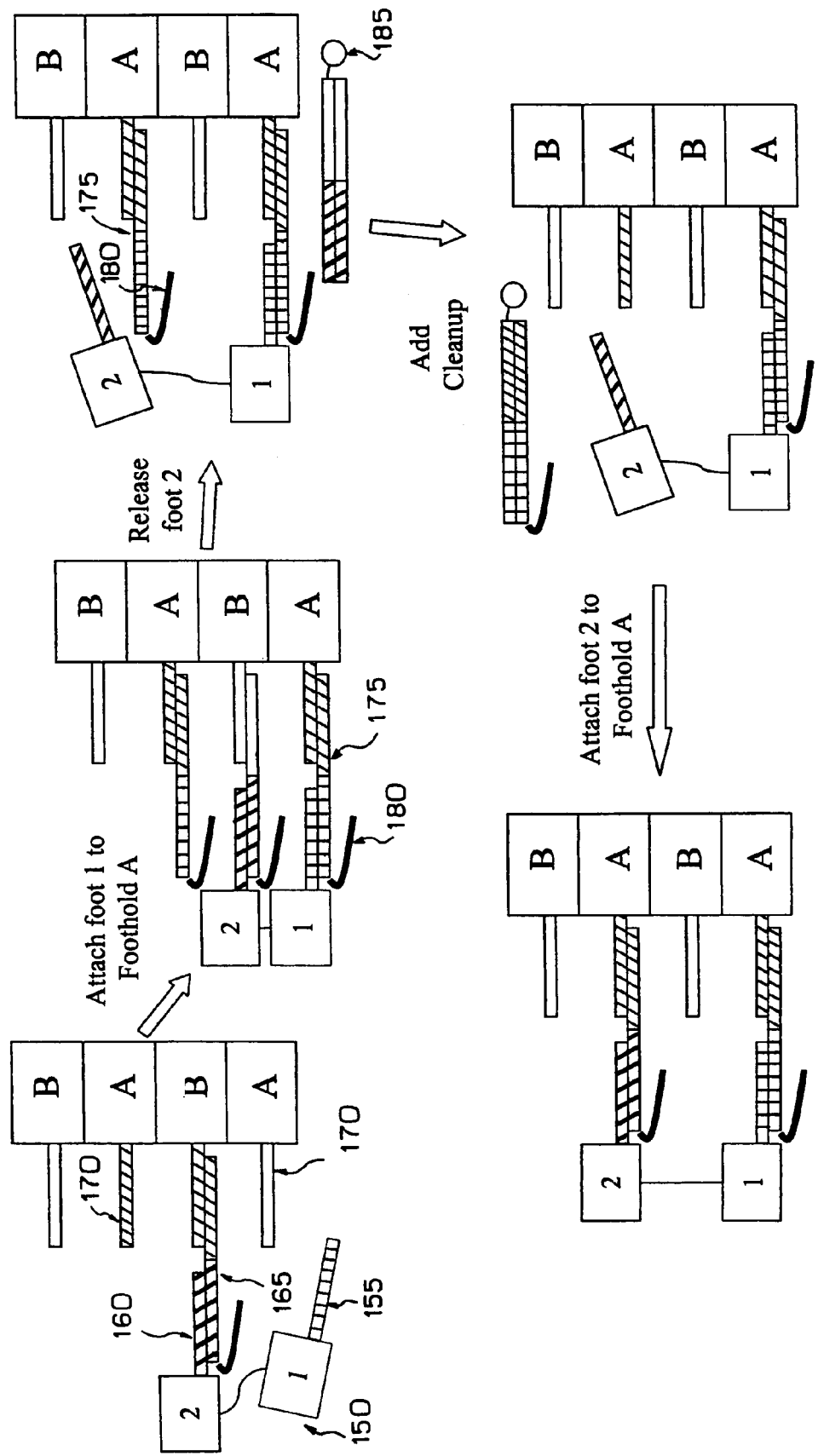
FIG. 10 shows a schematic illustration of using a cleanup molecule to permit a second foot of a biped to attach to a foothold identical in sequence to the foothold to which the first foot is already attached.

An alternative solution is shown in FIG. 10, where it is desired to place foot 2 (reference numeral 160) of biped 150 to a second foothold A (reference numeral 170) once foot 1 (reference numeral 155) is already attached to an identical first foothold A. The problem here is that a set molecule 175 with toehold 180 which was introduced when foot 155 was attached to foothold A, is already half bound to the second foothold A. A potential solution is to use a "cleanup" molecule to remove the interfering set molecule from the second foothold A without removing the identical set molecule holding foot 155 in attachment with the first foothold A. The "cleanup" molecule would be similar to an unset molecule except that it can only bind to the foot and foothold interacting portions of the target set molecule but not to the toehold itself. Therefore, the cleanup molecule cannot remove a set molecule which is already attached to a foot and foothold because it cannot initiate branch migration as no initial binding to a toehold occurs.

The unset and cleanup molecules in FIG. 10 are shown labeled with biotin 185. Biotin can be advantageously used to remove set molecules that have been detached with either an unset or cleanup molecule via magnetic beads coated with streptavidin to bind the set/unset and set/cleanup complexes, and can also be used to remove any unhybridized unset and cleanup molecules.

It will be appreciated by those of skill in the art that the different types of cohesion and the single or double strandedness of an end of a foot, a foothold, a set molecule or an unset molecule can be mixed and matched as long as the appropriate set and unset molecules are used for a given foot and foothold. For instance, the end of a foot can be in paranemic cohesion with a set molecule which also coheres to a foothold by Watson-Crick base pairing. Moreover, the different feet of a multiped and the different footholds of a molecular path do not all need to be single stranded or double stranded but can be a combination of single stranded feet and double stranded feet on the multiped and a combination of single stranded footholds and double stranded footholds on a molecular path.

Figure 11:
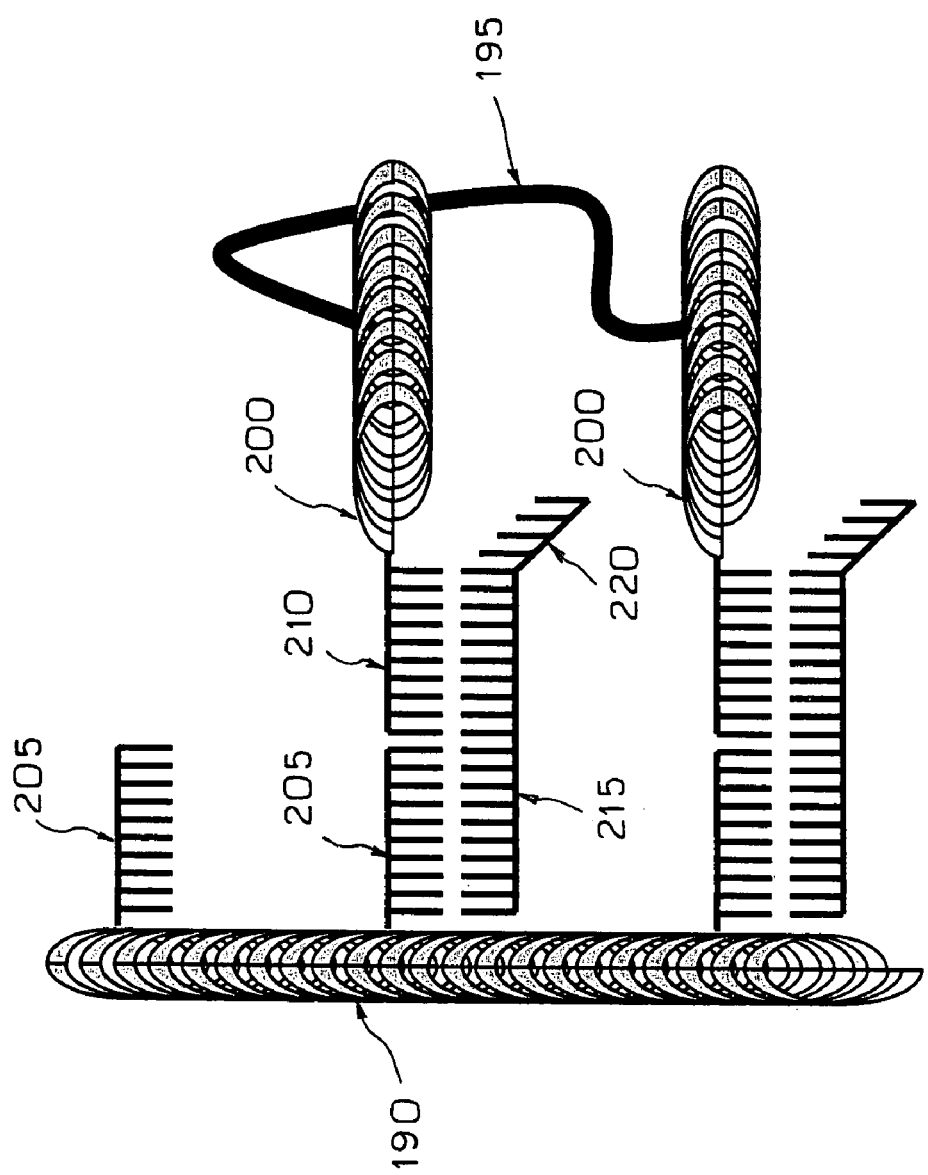
FIG. 11 shows a schematic illustration of a biped containing polypeptide α-helices derivatized with DNA attached to a molecular path containing polypeptide α-helices derivatized with DNA footholds.

Whereas the cohesion units, which are (1) the ends of the feet of a multiped, (2) the footholds of a molecular path, (3) the set molecules, and (4) the unset molecules of the nano-robotic system according to the present invention rely on sequence specificity of nucleic acids for the cycles of cohesion to regulate the steps traveled by the multiped along a molecular path, other elements in the nano-robotic system need not be constructed of nucleic acids. DNA, among other nucleic acids, can easily be attached to a wide variety of substrates via linkers, such as thiol, biotin, acrylic, and amino linkers that are commercially available (Integrated DNA Technologies, Coralville, Iowa). This allows key sequence specific cohesion units of the multiped and the molecular path to be linked to non-nucleic acid structural elements. In order to ensure the correct physical sequence of the feet and footholds, a solid support construction method remains most preferred although various other methods, such as template directed synthesis, are also suitable. When less flexibility in sections of the molecular path or in sections of the multiped is desired, any of numerous minimally flexible materials can be derivatized with nucleic acids. Non-limiting examples include polypeptide α-helices, nano-tubes, nano-rods, nano-crystals, polyalkynes, polysubstituted polyarenes, and patterned macroscopic surfaces. FIG. 11 presents a simplistic schematic illustration of an example of a nano-robotic system of the present invention with polypeptide α-helices derivatized with DNA ends of feet 210 and DNA footholds 205. An α-helical polypeptide molecular path 190 is derivatized with three single stranded DNA footholds 205 and the two α-helical polypeptide feet 200 are attached by an alkyl chain tether 195 and are each derivatized with a DNA end 210. Also shown in FIG. 11 are single stranded DNA set strands 215 (with toehold 220) which attach the single stranded DNA ends 210 of the biped feet to the single stranded DNA footholds 205 of the molecular path. A preferred embodiment of the present invention however is a nano-robotic system in which the multiped and molecular path are essentially composed of nucleic acids such as in the example illustrated in FIG. 2, where the psoralen molecules used for experimentally determining the position of the feet are the only non-nucleic acid components of the system.

It will also be appreciated by those of skill in the art that the tether used to link each foot of the multiped to at least one other foot on the multiped can be made of non-nucleic acid material although nucleic acid tethers are preferred. A wide variety of polymers are suitable for use as flexible tethers for the multiped. Aside from nucleic acids, suitable non-limiting examples include polyethers, substituted siloxane chains, alkyl chains, and polyethylene glycol chains. Alkyl and polyethylene glycol (PEG) are commercially available as alkyl or PEG phosphoramidites for DNA synthesis (IDT). In one embodiment of the nano-robotic system, the multiped itself can be tethered to the molecular path.

Figures 12A, 12B:
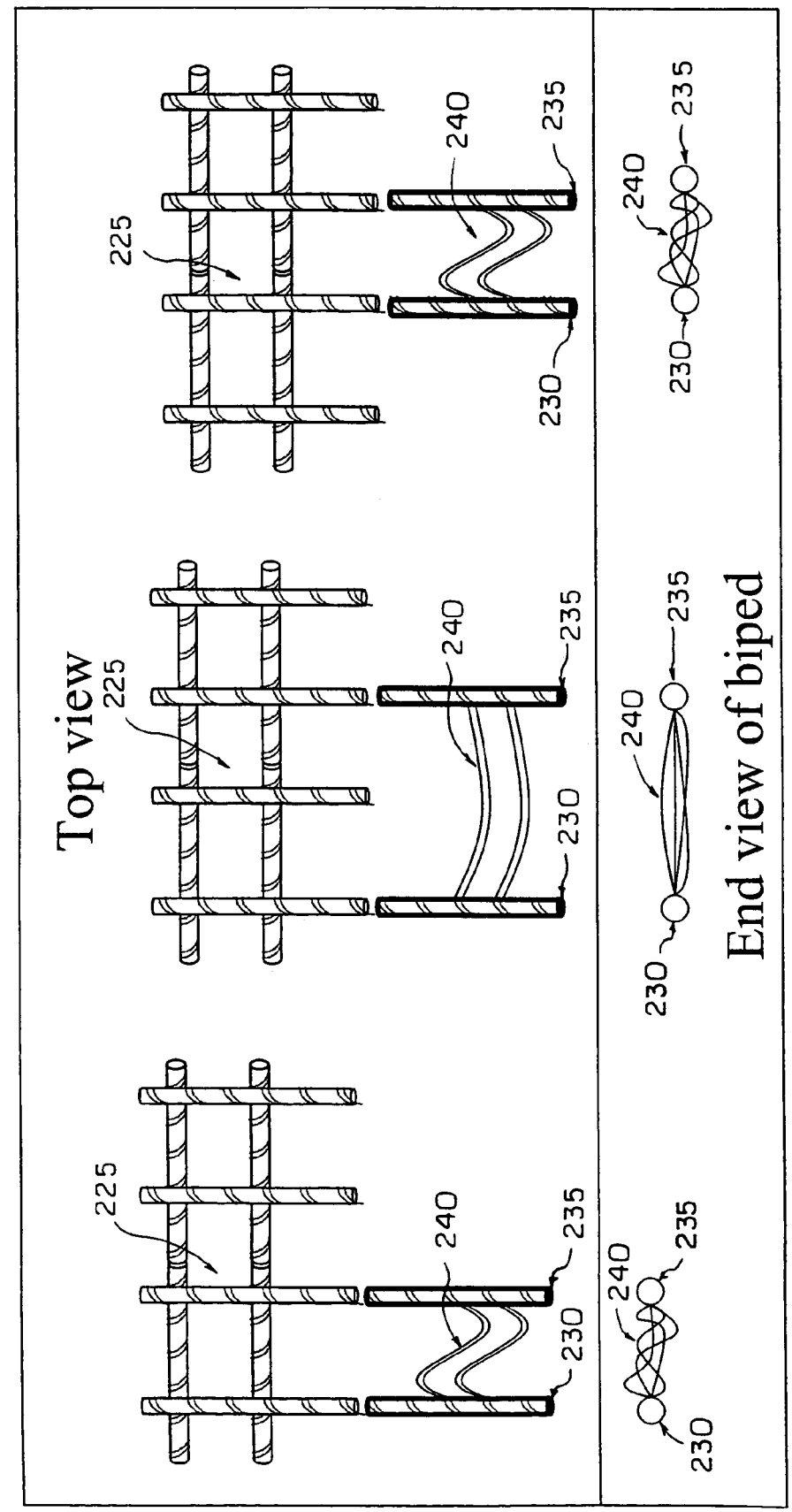
FIGS. 12A and 12B show schematic illustrations of a top view (FIG. 12A) and an end view (FIG. 12B) of a biped traveling along a molecular path using a sidling gait.
Figures 13A, 13B:
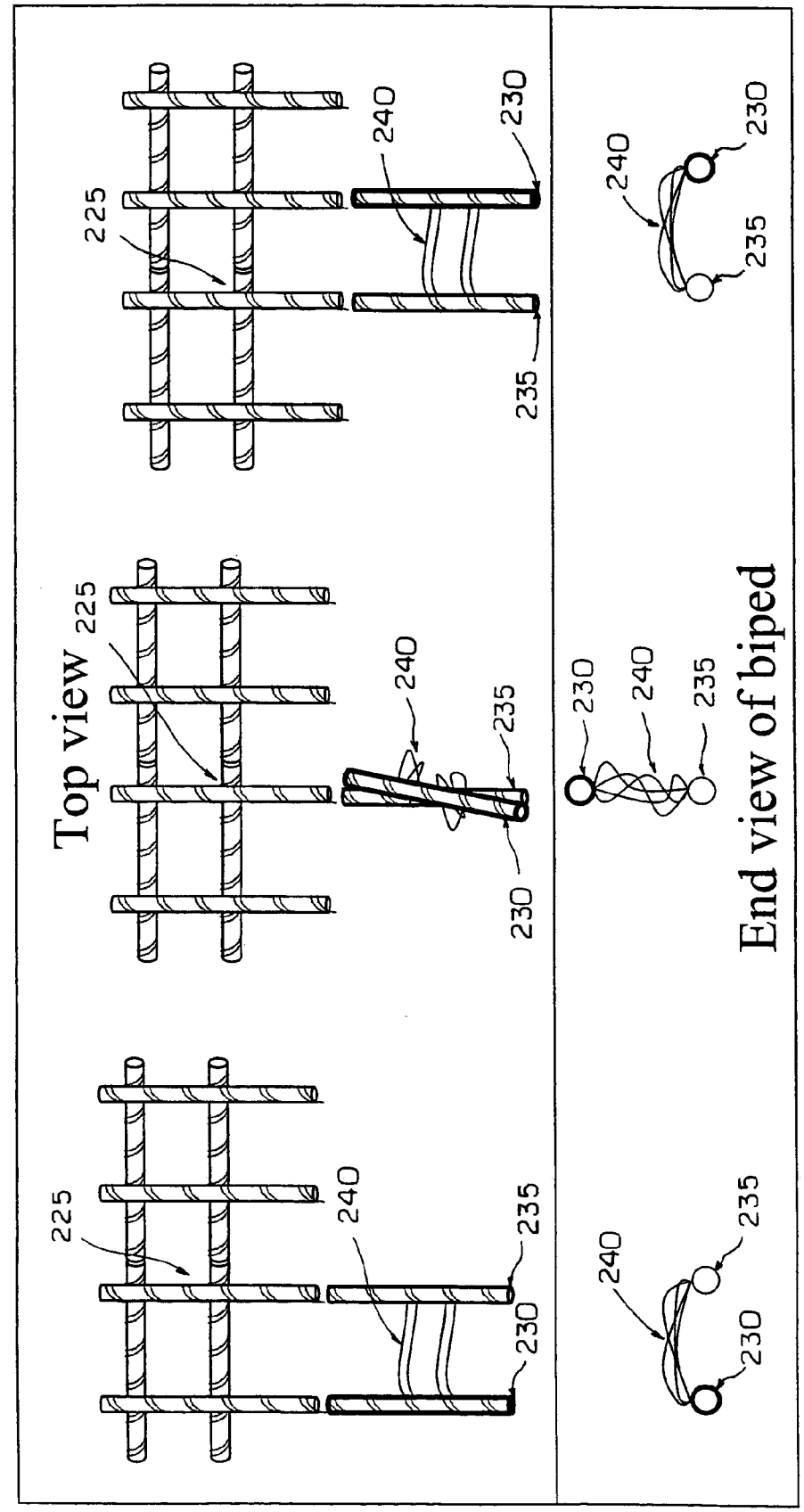
FIGS. 13A and 13B show schematic illustrations of a top view (FIG. 13A) and an end view (FIG. 13B) of a biped traveling along a molecular path using a rolling gait.

FIGS. 12A–12B and FIGS. 13A–13B show two different styles of traveling motion for a biped (with four tethers 240) on a molecular path 225. A top view and end view of a sidling gait are shown in FIGS. 12A and 12B, where there is a leading foot 235 and a trailing foot 230. Note that as shown in FIG. 12B, the flexible tethers 240 are attached to the inside of the feet and the feet do not pass by each other. By contrast, the rolling gait shown in FIGS. 13A–13B does not have a leading foot. Instead, foot 230 and foot 235 alternate passing one another in traveling along the molecular path. In the rolling gait, the flexible tethers 240 are attached to the tops of the feet (FIG. 13B). For a multiped, an inchworm style of motion, which may be considered to be a version of a sidling gait, is one of many ways in which a multiped larger than a biped can travel along a molecular path or along multiple molecular paths. It should be understood however that the concept of travel by the multiped along a molecular path may be relative. The molecular path can be thought of as being stationary relative to the multiped which is traveling on the molecular path or the molecular path can instead be thought of as moving relative to the multiped, such as shown in FIGS. 6A and 6B where there is relative motion between a minimally flexible biped and a flexible five arm junction.

Figure 14:
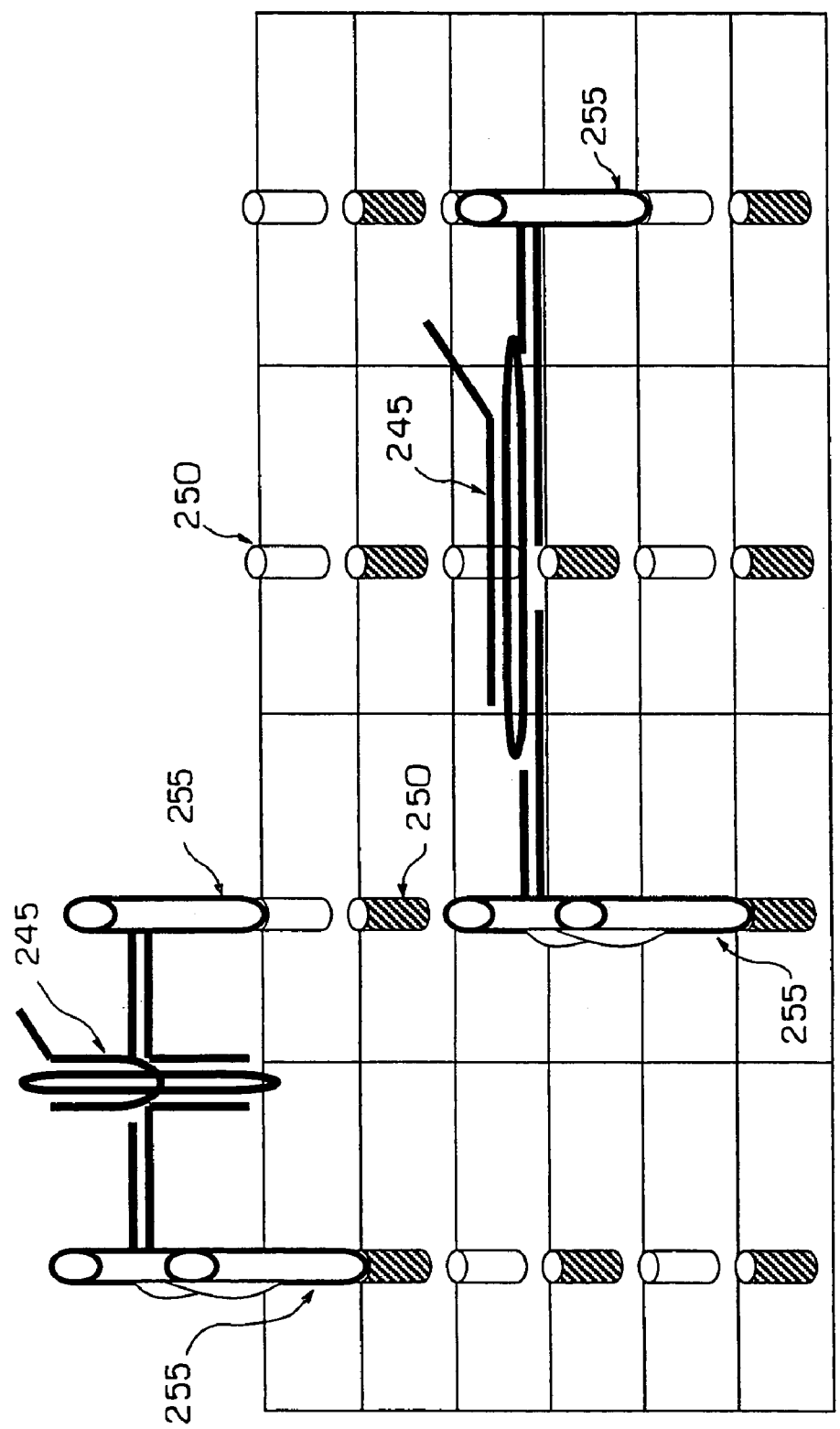
FIG. 14 shows a schematic illustration of two tripeds traveling on a two dimensional molecular path with footholds, where the feet are connected by a combination of flexible tethers and an extendible tether (or nano-actuator). One of the tripeds is shown to have the nano-actuator extended to skip over a foothold.

The tether does not necessarily need to be flexible. For instance, a tether can be an extendible linker that can be adjusted in discrete lengths to accommodate varying preset distances up to the length of the tether, i.e., the tether can expand and contract. FIG. 14 shows two tripeds traveling on a two dimensional molecular path with an array of footholds 250. Both tripeds have a combination of flexible tethers and an extendible tether 245 connecting their feet 255. One triped is shown with the extendible tether, i.e., nano-actuator, expanded to a discrete length so as to skip over a foothold and the other triped is shown with the extendible tether contracted to a different discrete length. By using extendible tethers adjusted for only certain discrete distances, control based on distance can be exercised over the selection of potential alternate footholds having the same sequence specificity. Examples of an extendible tether or nano-actuator are provided by Yurke et al. (2000) and Simmel et al. (2001, 2002).

Figure 15:
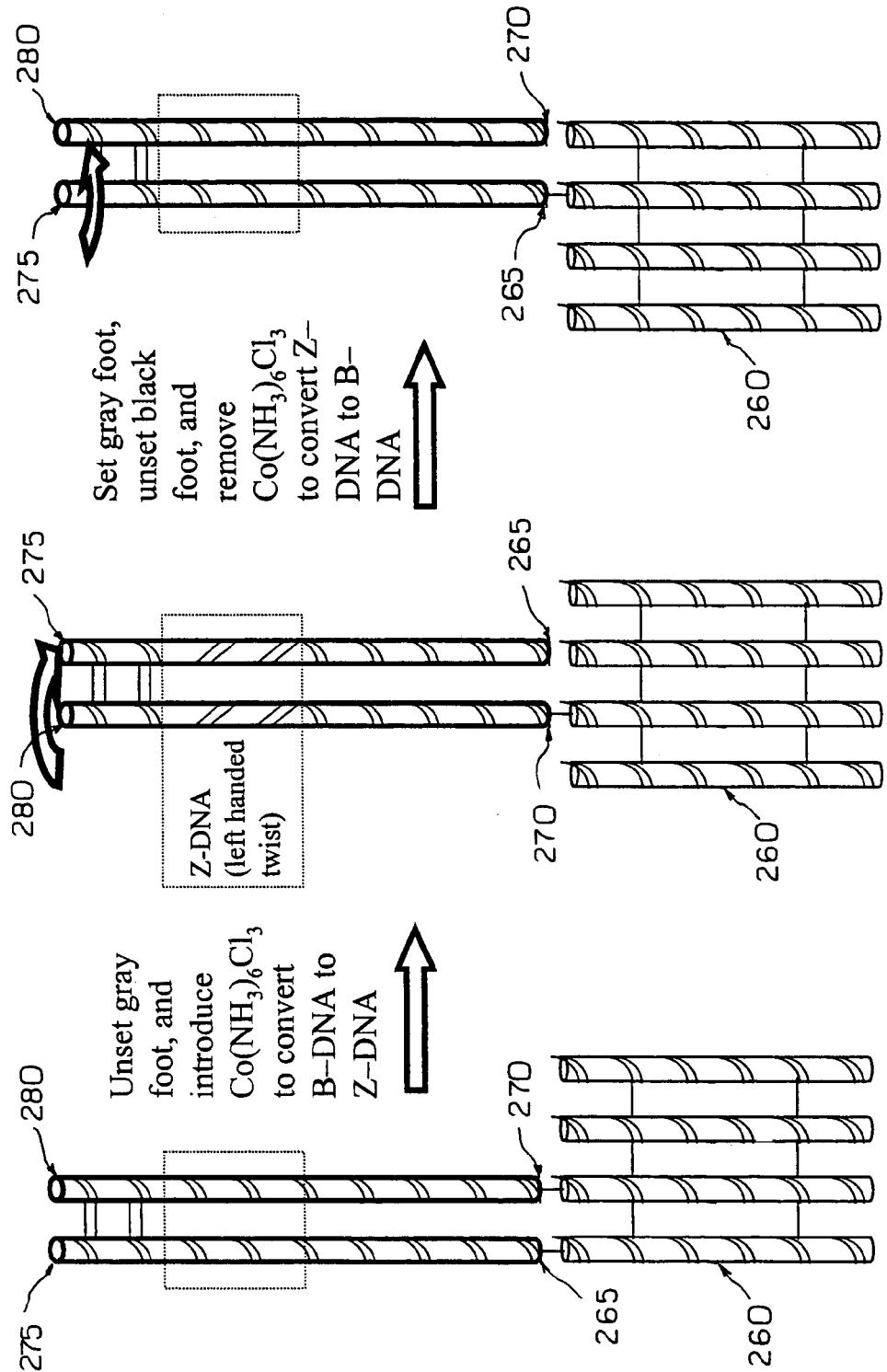
FIG. 15 shows a schematic illustration of a biped traveling along a molecular path using rotary motion generated by the B–Z DNA transition.

Another example of a tether which can regulate biped steps is based on generation of rotary motion by a B–Z transition of DNA (Mao et al., 1999). Certain sequences of DNA can undergo a transformation from standard B-DNA with a right handed twist to Z-DNA with a left-handed twist. This transition generates rotary motion which can regulate biped steps as depicted in FIG. 15, where a biped with the ends 265 and 275 of one foot and the ends 270 and 280 of the other foot have Z-DNA sequences separating them as shown.

The multiped in the nano-robotic system of the present invention can be used to carry molecules from point to point. Specific applications include:

1. Carrying a long molecule that acts as a conveyor-belt to transport molecules through a nano-factory for a series of synthetic steps.
2. Moving loads to and from various locations in a precisely controlled manner. Loads can be "picked up" and "put down" via numerous methods. Loads which have been derivatized with nucleic acid strands can be set down at a specific destination on the path, and, if need be, picked up later and moved again via set/unset strand exchanges.
3. "Threading" long polymers through small holes (down to ~20 nM in diameter, probably smaller if the polymer can be passed through a hole from one multiped to another), and/or winding them around long spindles. It should be noted that multipeds generally work in parallel so that multiple copies with the same sequence for the nucleic acid ends of the feet would typically be taking the same steps at once, while other copies with different sequences could be taking other steps.

The multiped can be a general-purpose transportation tool suitable for bearing a broad variety of loads. It can carry nano-particles, nano-tubes, nano-rods, liposomes, molecular components of various nano-machines, such as molecular circuit elements (e.g., Collier et al., 2001), molecular radio-wave resonant antennas (see "Remote electronic control of DNA hybridization through inductive coupling to an attached metal nanocrystal antenna" Hamad-Schifferli et al., 2002), molecular reactants, and nucleic acid nano-constructs. Additionally, a multiped can carry a molecular "string" connected to some fixed point (on or off the path). Some considerations on what can be carried are:

1. The load needs to be stable in a solvent where the nucleic acid is well behaved, e.g., typically a nearly neutral aqueous environment with mono- and di-valent cations present.
2. The load should not strongly react with the nucleic acids.
3. The Brownian forces experienced by the load should not be stronger than the binding forces of the multiped.

Having now generally described the invention, the same will be more readily understood through reference to the following example which is provided by way of illustration and is not intended to be limiting of the present invention.

EXAMPLE 1

Materials and Methods

Design: The DNA sequences of Watson-Crick pairing bases were designed using the program SEQUIN to assure sequence symmetry minimization as outlined in Seeman (1990). Special care was taken to minimize the likelihood that the set and unset strands would fold up on themselves. As far as possible, no more than three consecutive base-pairings will form if any of these strands should fold on itself. The last two bases on each foothold/dock strand are GT, and the first two on each foot strand are AC. This optimizes the psoralen intercalation and crosslinking reactions at the desired locations (Gia et al., 1992). Strand segments which were not intended to base-pair (primarily the flexible linkers) were made primarily of T's, which have the weakest possible combination of hydrogen bonding sites, and base-stacking potential. Table 1 below shows the actual sequences of each of the strands used. ψ represents psoralen and B represents biotin. The strands are listed 5' to 3'. See FIG. 2 for the structure formed by strands W1, W2, W3, D1, D2, D3, D4, D5, SS11, and SS22. The W strands form the biped, the D strands form the molecular path with three footholds/docks, the SS strands are set strands, and the US strands are unset strands.

TABLE 1

| | |
|---|---|
| W1 | ΨACATCTCACGTTAGGCCATCCATACTCGAGC SEQ ID NO: 1<br>CGTTCTCTTTTCTTATCTAGAATGAGTGACTG<br>CTGCGCTG |
| W2 | ΨACCATTAGACCAGCGCAGCATTTCTTTCTGA SEQ ID NO: 2<br>TGGCCTAA |

TABLE 1-continued

| | | |
|---|---|---|
| W3 | GAACGGCTCGAGTATGTCTTCTTTTGTCACTC ATTCTAGAT | SEQ ID NO: 3 |
| D1 | GTAAGGATAGAGTGGACACCGCAGACAAGGCG ATCTGGCGCTCCTGCCTTCATGCGTCATAGCG T | SEQ ID NO: 4 |
| D2 | GCATGAAGGCACCGATACACTGTTATTCCAGT | SEQ ID NO: 5 |
| D3 | CAGTGTATCGGACTCCTGAATCACACGGATCA CCAGGCCGACGAGAGGACTACTTCGATCCTAT TGTGCTCTGT | SEQ ID NO: 6 |
| D4 | ATAGGATCGAAGTAGTGGAGTGGAGCGCCAGA TCGCCTTGTCTGCGGACGCTCGT | SEQ ID NO: 7 |
| D5 | ACGAGCGTGGTATTTTTATACCTGTCCTGATC CGTGTGATTCACCTCTCGTCGGCCTGGACTCT ATCCTTAC | SEQ ID NO: 8 |
| SS11 | CAGCCAATCGTGAGATGTACGCTATGAC | SEQ TD NO: 9 |
| SS12 | CGCAAGGTCGTGAGATGTACTGGAATAA | SEQ ID NO: 10 |
| SS22 | GGCGTTGAGTCTAATGGTACTGGAATAA | SEQ ID NO: 11 |
| SS23 | GCCGAACCGTCTAATGGTACAGAGCACA | SEQ ID NO: 12 |
| US11 | BGTCATAGCGTACATCTCACGATTGGCTG | SEQ ID NO: 13 |
| US12 | BTTATTCCAGTACATCTCACGACCTTGCG | SEQ ID NO: 14 |
| US22 | BTTATTCCAGTACCATTAGACTCAACGCC | SEQ ID NO: 15 |
| US23 | BTGTGCTCTGTACCATTAGACGGTTCGGC | SEQ ID NO: 16 |

Synthesis and Purification: All DNA strands used were synthesized on an Expedite automatic DNA synthesizer, removed from the support and deprotected using routine phosphoramidite procedures. Psoralen was attached to the 5' end, when needed, by using Psoralen C2 Phosphoramidite (Glen Research). Similarly, commercial Biotin Phosphoramidite was used to add biotin to the 5' end of the unset strands. All strands were PAGE purified (stained with ethidium bromide and exposed briefly to UV for cutting). Care was taken at all times to minimize light exposure of the psoralenated strands prior to the psoralen activating UV exposure. Purified psoralenated strands all ran as single bands on denaturing gels.

Hybridization: All hybridization was carried out in TAE/Mg$^{2+}$ buffer (40 mM Tris-HCl (pH 8.0), 2 mM EDTA, 12.5 mM Magnesium Acetate). Equal amounts of the sidewalk (molecular path) and biped were initially annealed separately at 1 µM concentrations by slow cooling from 95° C. to room temperature over 48 hours in a 2-liter water bath in a Styrofoam box. The sidewalk and biped were combined with stoichiometric quantities of set strands 11 and 22 and placed in a 16° C. incubator for 30 minutes. All subsequent operations were carried out at 16° C. unless otherwise noted.

Unset procedure: Unset strands were added in 20% excess to the amount of set strand to be removed from the systems. The mixture was gently vortexed, and then left at 16° C. for 30 minutes. The solution was then added to a tube with streptavidin coated magnetic beads (roughly twice as much streptavidin as biotin). The system was allowed to sit for 25 minutes, and then the tube was placed on a magnetic stand, which pulled the beads to the side of the tube. The solution was then transferred to a new tube.

Set procedure: Set strands were added in stoichiometric quantities, gently vortexed, and given 30 minutes to form the appropriate connections. Aliquots were removed from the system as desired for subsequent analysis.

Psoralen Locking: Solutions to be analyzed via denaturing PAGE were transferred into cuvettes and exposed to UV light from a lamp with a peak wavelength at 365 nm. Exposure was carried out for 1 hour at 19° C.

Denaturing PAGE Analysis: The volume of each aliquot was doubled by adding denaturing dye (0.1% xylene cyanol FF tracking dye in 90% formamide with 1 mM EDTA, 10 mM NaOH). The samples were loaded onto denaturing gels containing 13% acrylamide (19:1 acrylamide:bisacrylamide) and 8 M urea in TBE (89 mM Tris-HCl, pH 8.0, 89 mM boric acid, 2 mM EDTA). Gels were run at 60° C. at roughly 35 V/cm and subsequently stained with Stainsall dye.

Results

Figure 16:
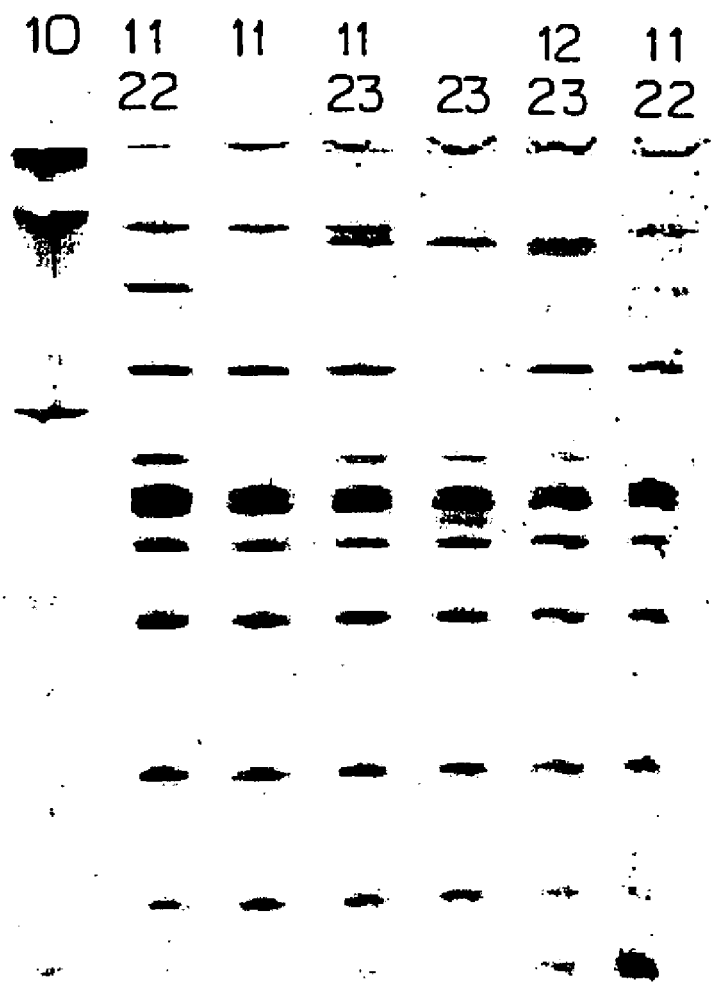
FIG. 16 is a PAGE gel (13% denaturing at 60° C.) showing the progress of the biped presented in FIG. 2 passing through each state 11,22; 11; 11,23; 23; and 12,23 and then finally returning to state 11,22 as illustrated in FIGS. 1A–1G. The bands in the boxed area clearly distinguish each state. The leftmost lane is a reference lane.

FIG. 16 presents the results of a denaturing polyacrylamide gel electrophoresis (PAGE), monitoring the progress of the biped as it traveled along the footholds of the molecular path by taking advantage of psoralen molecules on the ends of the two feet of the biped which reacted with neighboring nucleotides when exposed to ultraviolet light. The psoralen molecule can thus covalently link the foot, the set strand, and the foothold upon exposure to ultraviolet light. The biped, molecular path and set strands used in this experiment are shown in FIG. 2. Since all the strands (except the set strands) used to construct the biped and molecular path are of different lengths, a unique determination of where each foot is at a given time is made by PAGE. When the biped passes though each state, a sample aliquot is exposed to UV light, thereby causing the psoralen to link the feet of the biped to the footholds to which they are connected. Loading the aliquots onto a 13% polyacrylamide gel for denaturing PAGE clearly showed the progress of the biped on the molecular path. As can be seen in FIG. 16, the various states are distinguished on the basis of the distinctive bands in the boxed area of the gel. The gel in FIG. 16 provides confirmation that the biped traveled from state 11,22 (FIG. 1A) to state 11 (FIG. 1C) to state 11,23 (FIG. 1D) to state 23 (FIG. 1F), state 12,23 (FIG. 1G) and finally back to state 11,22. The bands shown in the boxed area migrated at the expected relative rates.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Allan V., Thompson H., and McNiven M., Motoring Around the Golgi, *Nature Cell Biology,* 4, p. E236 (October 2002)

Chan P, Glazer P., Triplex DNA: Fundamentals, advances, and potential applications for gene therapy, *J. Mol. Med.* 75(4), 267–282 (1997)

Collier C P, Jeppesen J O, Luo Y, Perkins J, Wong E W, Heath J R, Stoddart J F *JOURNAL OF THE AMERICAN CHEMICAL SOCIETY* 123 (50): 12632–12641 Dec. 19, 2001

Frank-Kamenetskii, M D, Mirkin S M, Triplex DNA Structures *Annu Rev Biochem* 64: 65–95 1995

Freier S. and Altmann K. -H., The ups and downs of nucleic acid duplex stability: structure-stability studies on chemically-modified DNA:RNA duplexes, *Nucleic Acids Research,* 25:4429–4443 (1997)

Gia, O., Magno, S., Garbesi, A., Colonna F., and Paumbo, M. Sequence specificity of psoralen photobinding to DNA: *A Quaantitative Approach. Biochemistry,* 31,1818–11822 (1992)

Hamad-Schifferli K, Schwartz J J, Santos A T, Zhang S G, Jacobson J M, *NATURE* 415 (6868): 152–155 Jan. 10, 2002

Hess H., Clemmens J., Matzke C, Bachand G, Bunker B. and Vogel V., Ratchet patterns Sort Molecular Shuttles, *Appl. Phys. A* 75, 309–313 (2002)

Hunter et al., New building blocks for the assembly of sequence selective molecular zippers, *Chem. Commun.,* 1642–1643 (2003)

Jaeger, L., Westhof, E. & Leontis, N. B. Tecto-RNA: Modular assembly units for the construction of RNA nano-objects. *Nucl. Acids Res.* 29, 455–463 (2001)

LaBean T., Yan H., Kopatsch J., Liu F., Winfree E., Reif J. H. and Seeman N. C., The Construction of DNA Triple Crossover Molecules, *Journal of the American Chemical Society* 122, 1848–1860 (2000).

Li X., Yang X., Qi J., and Seeman N., Antiparallel DNA Double Crossover Molecules as Components for Nanoconstruction, *Journal of the American Chemical Society,* 118, 6131–6140 (1996)

Liu F., Sha R., and Seeman N., Modifying the Surface Features of Two-Dimensional DNA Crystals, *J. Am. Chem. Soc.* 121, 917–922, (1999).

Mao C, Sun W., and Seeman N., Designed Two-Dimensional DNA Holliday Junction Arrays Visualized by Atomic Force Microscopy, *J. Am. Chem. Soc.* 121, 5437–5443 (1999a).

Mao C D, Sun W Q, Shen Z Y, et al. A Nanomechanical Device Based on the B-Z Transition of DNA, *Nature* 397 (6715): 144–146 (Jan. 14, 1999b).

Mathieu F., Mao C., Seeman N. C., *Journal of Biomolecular Structure & Dynamics,* 18, p.907 (2001).

Niemeyer C. and Adler M., Nanomechanical Devices Based on DNA, *Angew. Chem. Int. Ed.* 2002, 41, No. 20 p. 3779.

Seeman, N. C., De Novo design of sequences for nucleic acid structural engineering. *J. Biomol. Str. & Dyns.,* 8,573–581 (1990)

Simmel F., Yurke B., Using DNA to Construct and Power a Nanoactuator, *Physical Review E* 63 (4): art. no. 041913 Part 1 April 2001

Simmel, F. C. and Yurke, B., A DNA-based molecular device switchable between three distinct mechanical states, *Applied Physics Letters,* 80:(5)883–885 (2002)

Soong R., Bachand G., Neves H., Olkhovets A., Craighead H., and Montemagno C., Powering an Inorganic Nanodevice with a Biomolecular Motor, *Science,* 290, 1555, (24 Nov. 2000)

Yan H., Zhang X., Shen Z. and Seeman N. C., A Robust DNA Mechanical Device Controlled by Hybridization Topology, *Nature* 415, 62–65 (2002)

Yurke B., Turberfield A., Milils A. Jr., Simmel F., & Newmann J. A DNA-fuelled molecular machine made of DNA, *Nature* 406, 605–608 (2000).

Zhang X., Yan H., Shen Z., Seeman N., Paranemic cohesion of topologically-closed DNA molecules, *J. Amer. Chem. Soc.* 124,12940–12941 (2002).

What is claimed is:

1. A nano-robotic system comprising a molecular multiped, a molecular path along which the multiped can travel in more than one direction, a plurality of different sequence specific nucleic acid set molecules, and a plurality of different sequence specific nucleic acid unset molecules, said multiped comprising two or more feet, each of which has a sequence specific nucleic acid end and each of which is joined to at least one other foot on said multiped by a tether, said molecular path comprising a plurality of sequence specific nucleic acid footholds disposed along the path and to which individual nucleic acid foothold each foot of said multiped docks in the presence of a sequence specific nucleic acid set molecule that attaches by cohesion to both a sequence specific nucleic acid end of a foot of said multiped and a sequence specific nucleic acid foothold of said molecular path, said sequence specific nucleic acid set molecule comprising (1) a portion which is capable of attaching by cohesion to a sequence specific nucleic acid end of a foot of said multiped, (2) a portion which is capable of attaching by cohesion to a sequence specific nucleic acid foothold of said molecular path, and (3) a toehold portion which is incapable of separately attaching to either said sequence specific nucleic acid end of a foot of said multiped or said sequence specific nucleic acid foothold of said molecular path to which portion (1) or (2) of said sequence specific nucleic acid molecule can attach, wherein a foot that is docked to a foothold by a sequence specific nucleic acid set molecule is released from said foothold in the presence of a sequence specific nucleic acid unset molecule which strips away the sequence specific nucleic acid set molecule from said foot and said foothold, said sequence specific nucleic acid unset molecule being capable of attaching by cohesion to all of said portions (1), (2) and (3) of said sequence specific nucleic acid set molecule.

2. The nano-robotic system of claim 1, wherein said multiped is a biped.

3. The nano-robotic system of claim 1, wherein said tether is flexible.

4. The nano-robotic system of claim 1, wherein said tether is a nanoactuator.

5. The nano-robotic system of claim 1, wherein each of said two or more feet is joined to at least one other foot on said multiped by more than one tether.

6. The nano-robotic system of claim 1, wherein each of said two or more feet is joined to at least one other foot on said multiped by three tethers.

7. The nano-robotic system of claim 1, wherein each of said two or more feet is joined to at least one other foot on said multiped by four tethers.

8. The nano-robotic system of claim 1, wherein said tether is a nucleic acid.

9. The nano-robotic system of claim 1, wherein said multiped and said molecular path are tethered together.

10. The nano-robotic system of claim 1, wherein said sequence specific nucleic acid end of said two or more feet is single stranded.

11. The nano-robotic system of claim 1, wherein said sequence specific nucleic acid end of said two or more feet is double stranded.

12. The nano-robotic system of claim 1, further comprising one or more additional multipeds.

13. The nano-robotic system of claim 1, further comprising one or more additional molecular paths.

14. The nano-robotic system of claim 1, wherein said molecular path is a two dimensional array.

15. The nano-robotic system of claim 1, wherein said molecular path is a three dimensional array.

16. The nano-robotic system of claim 1, wherein said molecular path is a circular path.

17. The nano-robotic system of claim 16, wherein said circular path is a six helical bundle.

18. The nano-robotic system of claim 1, wherein said molecular path is an array of triple crossover nucleic acid molecules.

19. The nano-robotic system of claim 1, wherein said molecular path is an array of triple and double crossover nucleic acid molecules.

20. The nano-robotic system of claim 1, wherein said molecular path is an array of double crossover molecules.

21. The nano-robotic system of claim 20, wherein said double crossover molecules are selected from the group consisting of DAO, DAE, and a mixture of DAO and DAE molecules.

22. The nano-robotic system of claim 1, wherein said sequence specific nucleic acid foothold is single stranded.

23. The nano-robotic system of claim 1, wherein said sequence specific nucleic acid foothold is double stranded.

24. The nano-robotic system of claim 1, wherein the cohesion of said sequence specific nucleic acid set molecule to both a sequence specific nucleic acid end of a foot of said multiped and a sequence specific nucleic acid foothold of said molecular path is by Watson-Crick sequence complementarity.

25. The nano-robotic system of claim 24, wherein said sequence specific nucleic acid set molecule is single stranded and attaches to both a sequence specific single stranded nucleic acid end of a foot of said multiped and a sequence specific single stranded nucleic acid foothold of said molecular path.

26. The nano-robotic system of claim 25, wherein said sequence specific nucleic acid unset molecule is a single stranded nucleic acid molecule which is capable of attaching by cohesion in the form of sequence complementarity to all of said portions (1), (2) and (3) of said sequence specific nucleic acid set molecule.

27. The nano-robotic system of claim 1, wherein the cohesion of said sequence specific nucleic acid set molecule to both a sequence specific nucleic acid end of a foot of said multiped and a sequence specific nucleic acid foothold of said molecular path is by paranemic cohesion.

28. The nano-robotic system of claim 1, wherein the cohesion of said sequence specific nucleic acid set molecule to both a sequence specific nucleic acid end of a foot of said multiped and a sequence specific nucleic acid foothold of said molecular path is by triplex formation.

29. A method for positioning a foot of the multiped of the nano-robotic system of claim 1 from one foothold to another along the molecular path, comprising:

adding a sequence specific nucleic acid unset molecule to release a foot of the multiped off a first sequence specific nucleic acid foothold on the molecular path by stripping away a sequence specific nucleic acid set molecule attached by cohesion to both a sequence specific nucleic acid end of the foot of the multiped and the first sequence specific nucleic acid foothold, wherein the added sequence specific nucleic acid unset molecule initially attaches to portion (3) of the sequence specific nucleic acid set molecule by cohesion before stripping away the sequence specific nucleic acid set molecule; and adding a different sequence specific nucleic acid set molecule to complete a step of the foot onto a second sequence specific nucleic acid foothold on the molecular path, wherein the added sequence specific nucleic acid set molecule permits docking of the foot to the second foothold by cohesion with both the sequence specific nucleic acid end of the foot and the second sequence specific nucleic acid foothold.

* * * * *

UNITED STATES PATENT AND TRADEMARK OFFICE
CERTIFICATE OF CORRECTION

| | |
|---|---|
| PATENT NO. | : 7,163,794 B2 |
| APPLICATION NO. | : 10/962995 |
| DATED | : January 16, 2007 |
| INVENTOR(S) | : William B. Sherman and Nadrian C. Seeman |

It is certified that error appears in the above-identified patent and that said Letters Patent is hereby corrected as shown below:

In the Specification

Column 1, Lines 12-24 should read:
--STATEMENT REGARDING FEDERALLY SPONSORED RESEARCH OR DEVELOPMENT
This invention was made with government support under grant number GM029554 awarded by The National Institutes of Health, under grant numbers N00014-98-1-0093 and F30602-98-C-0148 awarded by the Department of Defense, and under grant numbers CTS9986512, EIA0086015, and CCR9725021 awarded by the National Science Foundation. The government has certain rights in the invention.--

Signed and Sealed this
Twenty-ninth Day of November, 2022

Katherine Kelly Vidal
*Director of the United States Patent and Trademark Office*